United States Patent
Sikora et al.

(10) Patent No.: US 10,736,681 B2
(45) Date of Patent: Aug. 11, 2020

(54) DEVICES, APPARATUSES, KITS, AND METHODS FOR OSTEOTOMY PLATES, GUIDES, AND CUTTERS

(71) Applicant: ARTHROSURFACE, INC., Franklin, MA (US)

(72) Inventors: George Sikora, Bridgewater, MA (US); Steven Ek, Bolton, MA (US); Tim Brightman, Franklin, MA (US); Carl Hasselman, Oakmont, PA (US)

(73) Assignee: ARTHROSURFACE, INC., Franklin, MA (US)

( * ) Notice: Subject to any disclaimer, the term of this patent is extended or adjusted under 35 U.S.C. 154(b) by 182 days.

(21) Appl. No.: 15/797,742

(22) Filed: Oct. 30, 2017

(65) Prior Publication Data

US 2018/0193034 A1 Jul. 12, 2018

Related U.S. Application Data

(60) Provisional application No. 62/416,153, filed on Nov. 1, 2016.

(51) Int. Cl.
*A61B 17/80* (2006.01)

(52) U.S. Cl.
CPC ........ *A61B 17/809* (2013.01); *A61B 17/8052* (2013.01)

(58) Field of Classification Search
CPC ... A61B 17/17; A61B 17/1703; A61B 17/171; A61B 17/1717; A61B 17/1725; A61B 17/1728; A61B 17/80; A61B 17/8004; A61B 17/8052; A61B 17/809
See application file for complete search history.

(56) References Cited

U.S. PATENT DOCUMENTS

| | | | | |
|---|---|---|---|---|
| 6,045,552 | A * | 4/2000 | Zucherman | A61B 17/1604 606/71 |
| 7,316,532 | B2 | 1/2008 | Matthys-Mark | |
| 8,911,445 | B2 * | 12/2014 | Rocci | A61B 17/1686 606/86 R |
| 9,345,493 | B2 * | 5/2016 | Nakaji | A61B 17/1695 |
| 9,955,964 | B2 * | 5/2018 | Mayer | A61B 17/0642 |
| 10,165,332 | B2 | 12/2018 | Rajaraman et al. | |
| 10,271,839 | B2 * | 4/2019 | Mayer | A61B 17/0642 |
| 2003/0228556 | A1 | 12/2003 | Giorno | |
| 2007/0173844 | A1 * | 7/2007 | Ralph | A61B 17/688 606/916 |
| 2009/0076617 | A1 * | 3/2009 | Ralph | A61B 17/688 623/17.19 |
| 2010/0241165 | A1 * | 9/2010 | Konieczynski | A61B 17/7071 606/248 |
| 2011/0087295 | A1 * | 4/2011 | Kubiak | A61B 17/1728 606/286 |
| 2012/0289964 | A1 * | 11/2012 | Nakaji | A61B 17/1695 606/80 |

(Continued)

*Primary Examiner* — Eric S Gibson
(74) *Attorney, Agent, or Firm* — Norton Rose Fulbright US LLP

(57) ABSTRACT

Embodiments are disclosed that relate generally to orthopedic treatments, and more particularly, but not by way of limitation, to devices, apparatuses, kits, and methods for an orthopedic device comprising one or more osteotomy plates, guides, and/or cutters (e.g., for bunion removal or for stabilizing a joint or a cut/break line of a fracture).

20 Claims, 30 Drawing Sheets

(56) References Cited

U.S. PATENT DOCUMENTS

2013/0267955 A1* 10/2013 Kubiak .................. A61B 17/80
  606/70
2013/0325073 A1    12/2013 Sikora et al.
2014/0214037 A1*  7/2014 Mayer ................ A61B 17/0642
  606/75
2018/0193034 A1*  7/2018 Sikora .................. A61B 17/151

* cited by examiner

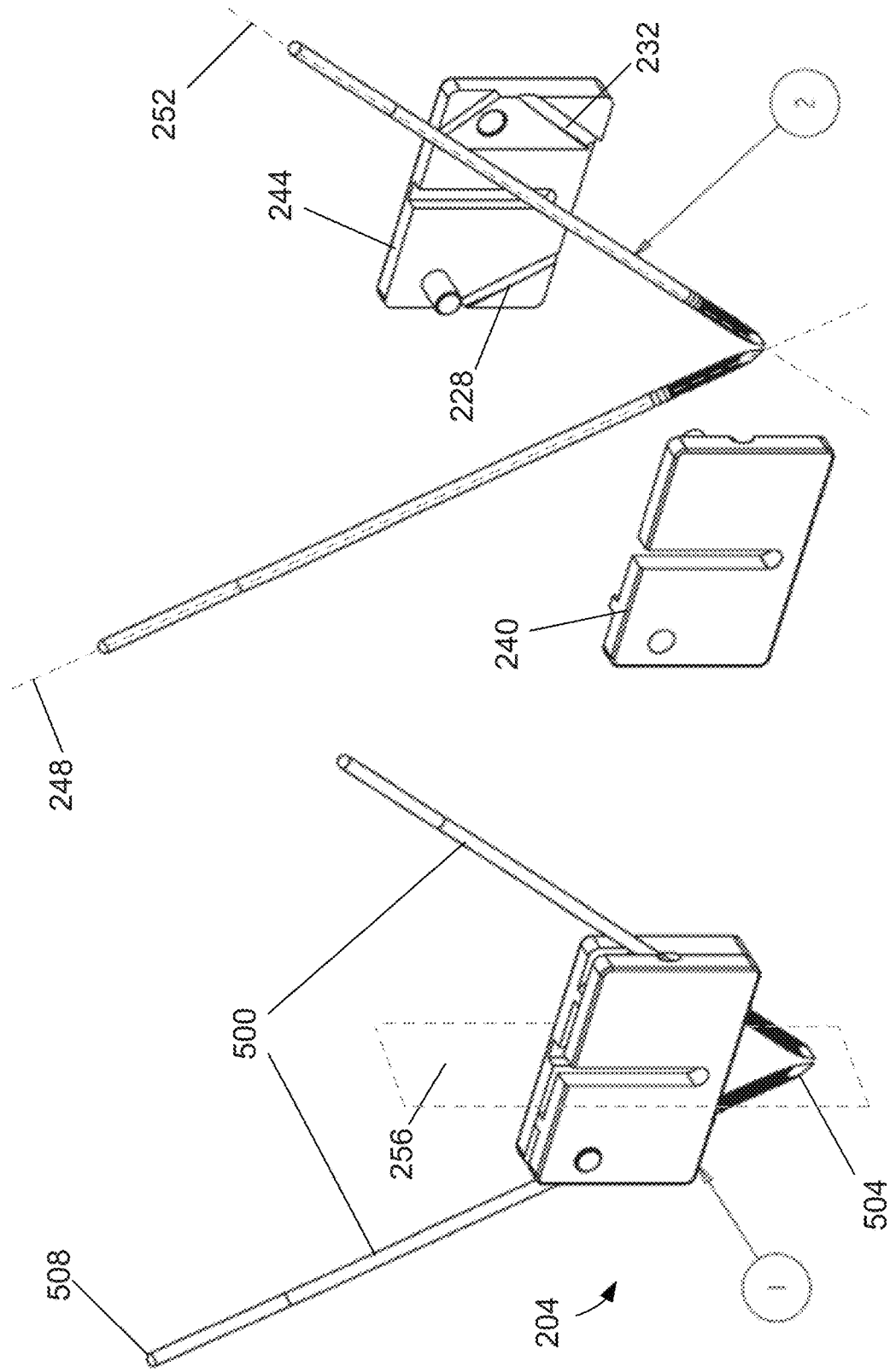

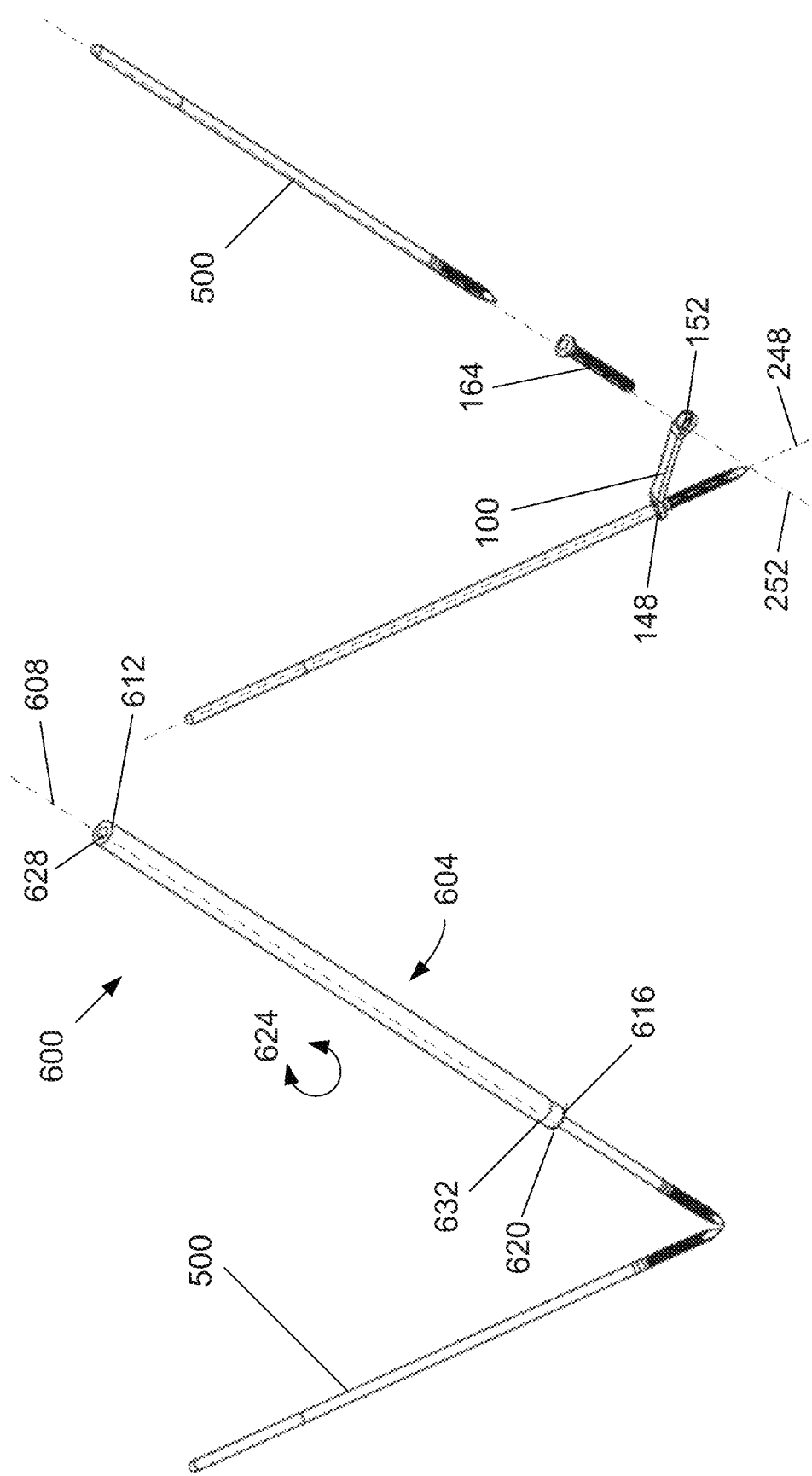

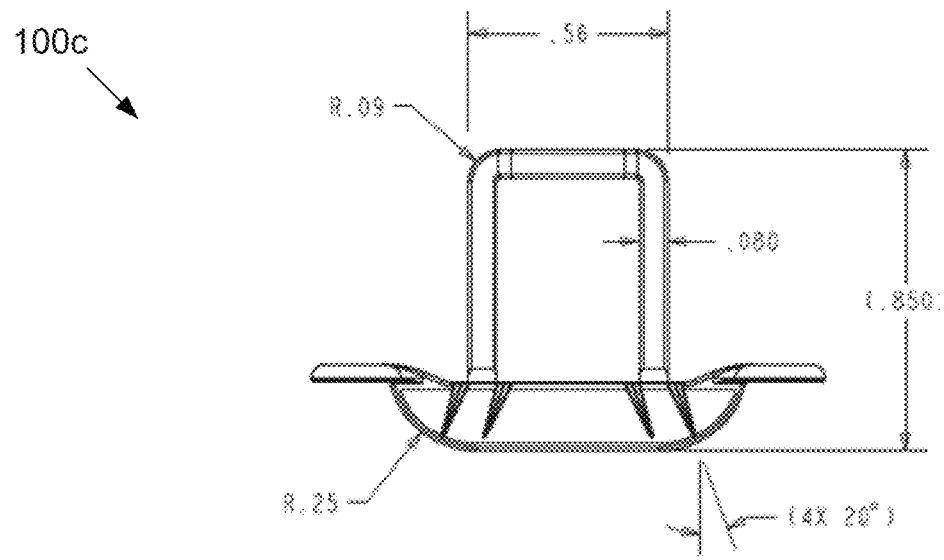
FIG. 10D
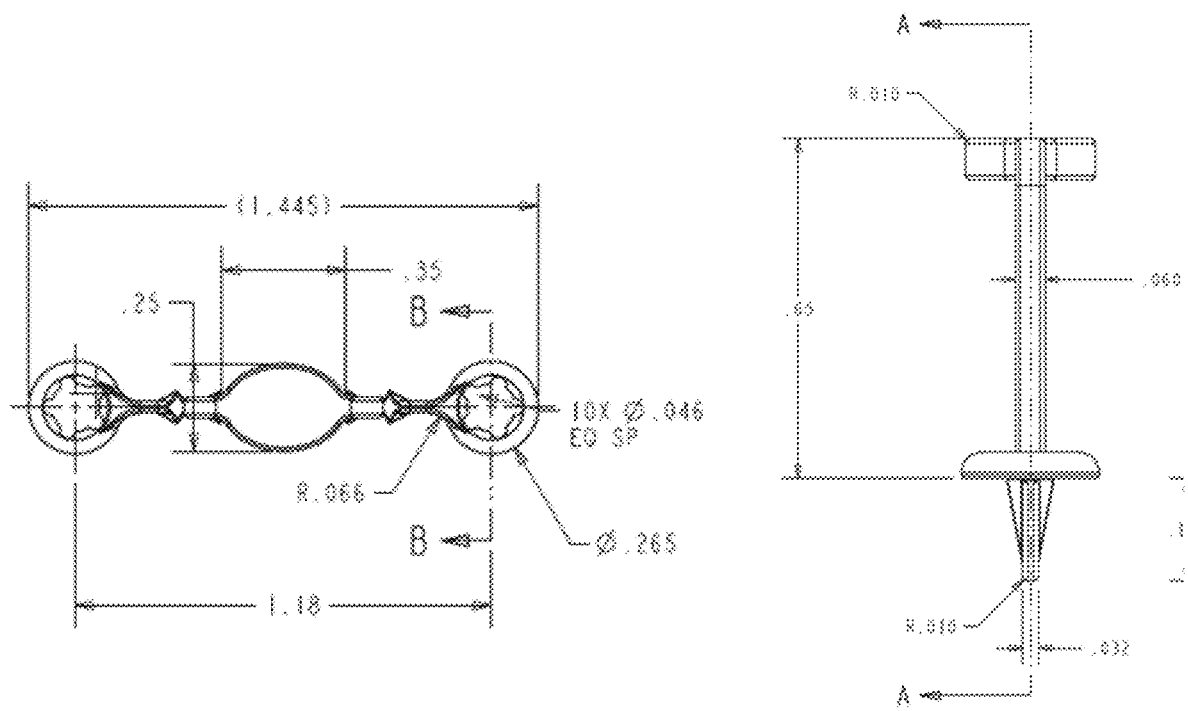
FIG. 10E
FIG. 10F

DEVICES, APPARATUSES, KITS, AND METHODS FOR OSTEOTOMY PLATES, GUIDES, AND CUTTERS

CROSS-REFERENCE TO RELATED APPLICATION

This application claims the benefit of U.S. Provisional Application No. 62/416,153, filed Nov. 1, 2016, the content of each of which application is incorporated herein by reference in its entirety.

BACKGROUND

1. Field of the Invention

The present invention relates generally to orthopedic treatments, and more particularly, but not by way of limitation, to devices, apparatuses, kits, and methods for an orthopedic device comprising one or more osteotomy plates, guides, and/or cutters (e.g., for bunion removal).

2. Description of Related Art

Examples of orthopedic fasteners that can be used for an osteotomy are disclosed in (1) U.S. patent application Ser. No. 10/165,332, filed Jun. 7, 2002 and published as Pub. No. US 2003/0228556, and (2) U.S. patent application Ser. No. 13/793,759 filed Mar. 11, 2013 and published as Pub. No. US 2013/0325073. Another example of an orthopedic fastener is disclosed in U.S. Pat. No. 7,316,532.

SUMMARY

This disclosure includes embodiments of devices, apparatuses, kits, and methods for an orthopedic device comprising one or more osteotomy plates, guides, and cutters (e.g., for bunion removal, such as, for example, via chevron bunionectomy, or for bone repair of a fracture). For example, at least some of the present embodiments include an elongated implant body having a portion that extends below lower bone-facing surfaces of guide members on either end of the implant body. As described in more detail below, such an implant body can extend into a slot that is cut into and across a seam between first and second bone portions while fasteners secure the guide members relative to the respective first and second bone portions. In this way, at least some embodiments of the present implants can be secured to the bone to resist vertical movement of the implant relative to the bone portions and to resist horizontal separation of the bone portions, while the elongated body member resists rotation and lateral movement of the bone portions relative to each other. In this way, at least some embodiments of the present implants is configured to (1) resist relative movement between the bone segments, and (2) distribute forces on the implant over a relatively larger surface area to reduce maximum point loads and stresses on the bone portions and the implant, both in a way and to a greater degree than has previously been possible with prior art implants.

Some embodiments of the present bone-implant apparatuses comprise: an elongated implant body having a first end and an opposing second end; a first guide member coupled to the first end of the implant body, the first guide member having a lower bone-facing surface and defining a first fastener hole that extends through the bone-facing surface; and a second guide member coupled to the second end of the implant body, the first guide member having a lower bone-facing surface and defining a second fastener hole that extends through the bone-facing surface; where a lower portion of the implant body extends below at least a portion of the lower bone-facing surface of the first guide member and/or below at least a portion of the lower bone-facing surface of the second guide members.

In some embodiments of the present bone-implant apparatuses, a lower portion of the implant body extends below the lower bone-facing surfaces of both of the first and second guide members. In some embodiments, the lower bone-facing surface of the first guide member is coplanar with the lower bone-facing surface of the second guide member. In some embodiments, a lower edge of the implant body is curved. In some embodiments, the implant body is substantially planar. In some embodiments, a central plane of the implant body is perpendicular to a plane of the bone-facing surface of the first guide member and/or is perpendicular to a plane of the bone-facing surface of the second guide member.

In some embodiments of the present bone-implant apparatuses, the implant body has an upper edge, a lower edge opposing the upper edge, a pair of opposing sides extending between the upper and lower edges, a length extending between the first and second ends, a height extending between the upper and lower edges, and a width extending between the opposing sides. In some embodiments, the length of the implant body is greater than the height of the implant body, and the height of the implant body is greater than the width of the implant body. In some embodiments, the width of the implant body is greater than the height of the implant body.

In some embodiments of the present bone-implant apparatuses, the first fastener hole has a central axis, the second fastener hole has a central axis, and the orientation of each of the first and second guide members is substantially fixed relative to the implant body. In some embodiments, the central axis of the first fastener hole extends toward a lateral plane that bisects the implant body, and the central axis of the second fastener hole extends toward the lateral plane. In some embodiments, the central axis of the first fastener hole intersects the central axis of the second fastener hole. In some embodiments, the central axis of the first fastener hole intersects the central axis of the second fastener hole at the lateral plane. In some embodiments, the lower edge is straight, curved, and/or arcuate.

In some embodiments of the present bone-implant apparatuses, the first and second fastener holes are each configured to receive a fastener coaxial with the respective central axis.

In some embodiments of the present bone-implant apparatuses, the implant body defines one or more holes extending between the pair of opposing sides.

In some embodiments of the present bone-implant apparatuses, at least one of the first and second guide members defines a plurality of fastener holes. In some embodiments, the first guide member defines a plurality of first fastener holes, and the second guide member defines a plurality of second fastener holes.

In some embodiments of the present bone-implant apparatuses, the central axis of the first fastener hole is substantially parallel to the central axis of the second fastener hole. In some embodiments, the first guide member is configured to be bent relative to the implant body when the apparatus is secured to a bone, and the second guide member is configured to be bent relative to the implant body when the apparatus is secured to a bone.

Some embodiments of the present bone-implant apparatuses further comprise a handle configured to be detachably coupled to the implant body. In some embodiments, the handle comprises one or more cross-members and one or more attachment members, and where the attachment members are configured to couple the handle to the implant body via one or more detachable joints.

Some embodiments of the present bone-implant apparatuses further comprise: one or more barbs disposed on one or more of the opposing sides and configured to compress one or more pieces of bone together. In some embodiments, each barb is tapered such that a width of the barb is greater at the upper edge of the implant body and decreases as the barb extends toward the lower edge of the implant body. In some embodiments, each barb extends at an angle away from a lateral plane that bisects the implant body such that a distance between the barb and the lateral plane increases as the barb extends toward the lower edge of the implant body.

Some embodiments of the present bone-implant apparatuses further comprise multiple implant bodies coupled together by a third guide member defining a third fastener hole having a central axis, where the multiple implant bodies extend in a direction of a length of the implant bodies.

In some embodiments of the present bone-implant apparatuses, the implant body comprises a metal, a plastic, or a composite material. In some embodiments, at least a portion of an exterior surface of the body is porous. In some embodiments, the at least a portion of the exterior surface is configured to be osteoconductive and/or osteoinductive.

Some embodiments of the present guide apparatuses comprise: a guide body having a guide head and a handle coupled to the guide head, the guide head having a first end, a second end opposing the first end, an upper side, a lower side opposing the upper side, and a pair of opposing lateral sides extending between the upper and lower sides, the guide head defining: a first guide pin channel extending through the lower side of the guide head, a second guide pin channel extending through the lower side of the guide head, and a saw guide channel between the first guide pin channel and the second guide pin channel and extending through the lower side of the guide head; where the first guide pin channel has a central axis that extends perpendicular to the lower side, and the second guide pin channel has a central axis that extends perpendicular to the lower side; and where the guide head is configured to be temporarily coupled to a bone by guide pins extending through the first and second guide pin channels into the bone such that: the lower side of the guide body faces the bone; and a saw blade can be guided along the saw guide channel to form a recess in the bone.

In some embodiments of the present guide apparatuses, the guide head further defines a slot disposed in at least one of the lateral sides at the lower side of the guide head, where a length of the slot extends in a direction parallel to the lower side of the guide head. In some embodiments, the slot partially extends along at least one of the lateral sides in a direction parallel with the lower end, the slot having a blocking surface spaced above the lower side such that the blocking surface is configured to contact the shaft to limit the depth to which the saw blade can form the recess in the bone.

Some embodiments of the present guide apparatuses further comprise: a saw comprising the saw blade, the saw blade being a circular saw blade that can be rotated via a shaft that is coupled to the circular saw blade, where the shaft extends through the slot when the circular saw blade is disposed in the saw guide channel. In some embodiments, the saw blade has a plurality of cutting surfaces and a plurality of notches disposed on an outer perimeter of the saw blade, where the notches each have a short edge and a long edge. In some embodiments, the short edge is disposed at an angle acute with a diameter of the saw blade and an angle obtuse with the long edge.

In some embodiments of the present guide apparatuses, the first guide pin channel also extends through the upper side of the body. In some embodiments, the second guide pin channel also extends through the upper side of the body.

In some embodiments of the present guide apparatuses, the handle is coupled to one of the lateral sides of the guide head and extends away from the guide head at an angle from the plane of the lateral side. In some embodiments, the guide head is a unitary piece.

Some embodiments of the present guide apparatuses comprise: a guide body having a first end, a second end opposing the first end, an upper side, a lower side opposing the upper side, and a pair of opposing lateral sides extending between the upper and lower sides, the body defining: a first guide pin channel extending through the lower side of the body, a second guide pin channel extending through the lower side of the body, and a saw guide channel extending through the lower side of the body; where the first guide pin channel has a central axis that extends toward a lateral plane that bisects the guide body, and the second guide pin channel has a central axis that extends toward the lateral plane; and where the body is configured to be temporarily coupled to a bone by guide pins extending through the first and second guide pin channels into the bone such that: the lower side of the guide body faces the bone; and a saw blade can be guided along the saw guide channel to form a recess in the bone.

In some embodiments of the present guide apparatuses, the guide body further defines a slot extending through at least one of the lateral sides into and parallel with the saw guide channel.

In some embodiments of the present guide apparatuses, the saw blade is a circular saw blade that can be rotated via a shaft that is coupled to the circular saw blade and extends through the slot when the circular saw blade is disposed in the saw guide channel. In some embodiments, the slot partially extends vertically along at least one of the lateral sides from the upper side toward the lower side, the slot having a lower end spaced above the lower side other body such that the body is configured to contact the shaft to limit the depth to which the saw circular saw blade can form the recess in the bone.

In some embodiments of the present guide apparatuses, the first guide pin channel also extends through the first end of the body. In some embodiments, the second guide pin channel also extends through the second end of the body.

In some embodiments of the present guide apparatuses, the saw guide channel also extends through the upper side of the body such that the saw blade can be inserted into the saw guide channel through the upper side of the body.

In some embodiments of the present guide apparatuses, the saw guide body comprises two pieces that cooperate to define the first guide pin channel, the second guide pin channel, and the saw guide channel. In some embodiments, the two pieces are configured to detach from each other to decouple the guide body from guide pins extending through the guide pin channels into a bone without removing the guide pines from the bone.

Some embodiments of the present guide apparatuses further comprise: a reamer having a body extending outwardly relative to a rotational axis, the body having a proximal cutting end, a distal end, and defining a hollow channel extending through the body from the proximal end to the distal end along the rotational axis; where the reamer is configured to be disposed over a guide pin extending into a bone such that the guide pin extends through the hollow channel and the reamer can be rotated around the guide pin with the proximal cutting end in contact with a surface of the bone to form a recess in the bone.

Some embodiments of the present kits comprise: an embodiment of the present guide apparatuses; and a package within which the guide apparatus is sealed. Some embodiments further comprise a saw blade (e.g., a circular saw blade). In some embodiments, a shaft is coupled to the circular saw blade. Some embodiments further comprise: one or more guide pins. Some embodiments further comprise: one or more fasteners. Some embodiments of the present kits further comprise: an embodiment of the present bone-implant apparatuses.

Some embodiments of the present kits comprise: an embodiment of the present bone-implant apparatuses; and a package within which the apparatus is sealed.

Some embodiments of the present methods (e.g., of modifying a bone) comprise: forming a recess in the bone with a saw blade that is disposed in a saw guide channel of a guide body of a guide apparatus that has the lower end of the guide body facing the bone and guide pins extending through the first and second guide pin channels of the guide body into the bone.

In some embodiments of the present methods, a first one of the guide pins that extends through the first guide pin channel is disposed on a first side of a cut or break line in the bone, and a second one of the guide pins that extends through the second guide pin channel is disposed on a second side of the cut or break line in the bone.

Some embodiments of the present methods further comprise: positioning the bottom of the guide body of the guide apparatus against the surface of the bone; and inserting the guide pins through the first and second guide pin channels of the guide body into the bone. Some embodiments further comprise: decoupling the guide body from the guide pins while the guide pins are inserted into the bone. In some embodiments, decoupling the guide body comprises detaching from each other two pieces of the guide body that cooperate to define the first guide pin channel, the second guide pin channel, and the saw guide channel.

Some embodiments of the present methods further comprise: disposing at least a portion of an embodiment of the present bone-implant apparatuses into the recess.

Some embodiments of the present methods further comprise: rotating a reamer around a first one of the guide pins with the proximal cutting end of the reamer in contact with the bone to enlarge a first end of the recess. Some embodiments further comprise: rotating a reamer around a second one of the guide pins with the proximal cutting end of the reamer in contact with the bone to enlarge a second end of the recess. Some embodiments further comprise: disposing at least a portion of an embodiment of the present bone-implant apparatuses into the recess, with at least a portion of the implant body in a central portion of the recess, at least a portion of the first guide member in the enlarged first end of the recess, and at least a portion of the second guide member in the enlarged second end of the recess.

Some embodiments of the present methods further comprise: inserting a first fastener through the first fastener hole of the bone-implant apparatus and into a first hole in the bone; and inserting a second fastener through the second fastener hole of the bone-implant apparatus and into a second hole in the bone. In some embodiments, the first fastener extends through a first part of the bone, across a cut or break line in the bone, and into a second part of the bone. In some embodiments, the second fastener extends through the second part of the bone, across the cut or break line, and into the first part of the bone. In some embodiments, the first hole in the bone is a hole from which a first one of the guide pins was removed, and/or the second hole in the bone is a hole from which a second one of the guide pins was removed.

Some embodiments of the present methods comprise: inserting a first fastener through a first fastener hole of an embodiment of the present bone-implant apparatuses and into a first part of a bone; and inserting a second fastener through the second fastener hole of the bone-implant apparatus and into a second part of the bone; where the first and second parts of the bone are separated by a cut or break line; and where at least a portion of the bone-implant apparatus is disposed in a recess in the bone, the recess spanning the cut or break line. In some embodiments, the recess includes an elongated middle portion in which at least a portion of the implant body of the bone-implant apparatus is disposed, an enlarged first end in which at least a portion of the first guide member of the bone-implant apparatus is disposed, and an enlarged second end in which at least a portion of the second guide member of the bone-implant apparatus is disposed.

Some embodiments of the present methods comprise: inserting an elongated implant body of a bone-implant apparatus into a slot cut into and across a seam between first and second bone portions (e.g., the bone-implant apparatus comprising: a first guide member coupled to a first end of the implant body, the first guide member having a lower bone-facing surface and defining a first fastener hole that extends through the bone-facing surface; and a second guide member coupled to a second end of the implant body, the first guide member having a lower bone-facing surface and defining a second fastener hole that extends through the bone-facing surface; where a lower portion of the implant body extends below the lower bone-facing surface of at least one of the first and second guide members); securing the first guide member to the first bone segment such that the lower bone-facing surface of the first guide member faces the first bone segment; and securing the second guide member to the second bone segment such that the lower bone-facing surface of the second guide member faces the second bone segment.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any embodiment of the present devices, apparatuses, kits, and methods, the term "substantially" may be substituted with "within [a percentage] of" what is specified, where the percentage includes 0.1, 1, 5, and/or 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus or kit that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Further, an apparatus, device, or structure that is configured in a certain way is configured in at least that way, but it can also be configured in other ways than those specifically described.

Any embodiment of any of the present devices, apparatuses, kits, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiments depicted in the figures.

FIGS. 5A-5D depict various views of stages of the present methods using the saw guide of FIGS. 3A-3C with the osteotomy implant of FIGS. 1A-1F.

FIGS. 10A-10L depict various views of a fourth embodiment of the present osteotomy implants.

DESCRIPTION OF ILLUSTRATIVE EMBODIMENTS

Figure 1A:
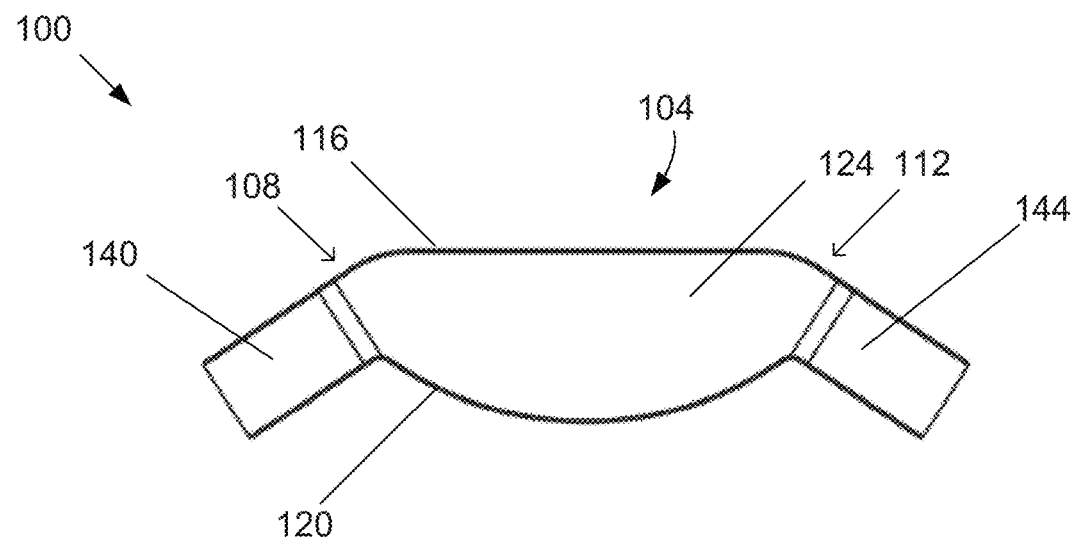
FIGS. 1A-1F depict various views of a first embodiment of the present osteotomy implants.
Figure 1B:
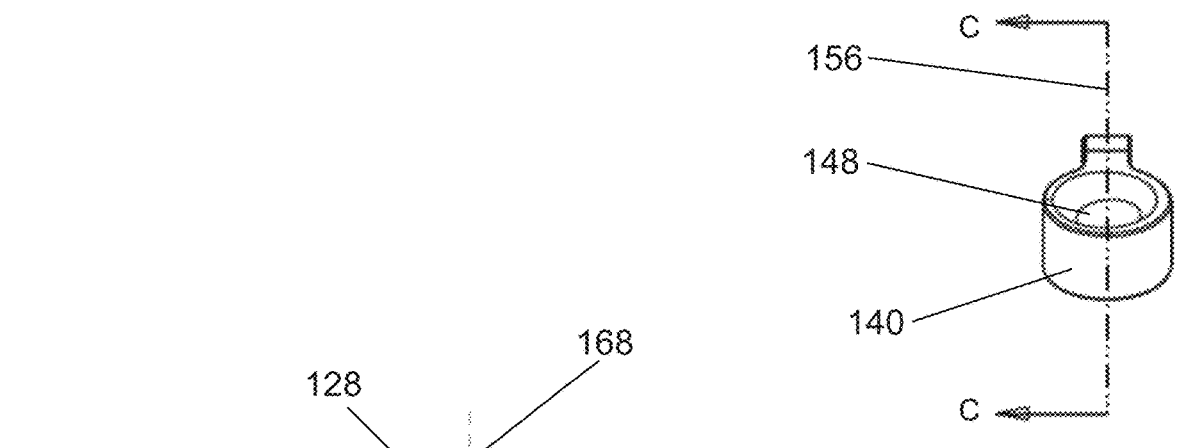
Figure 1C:
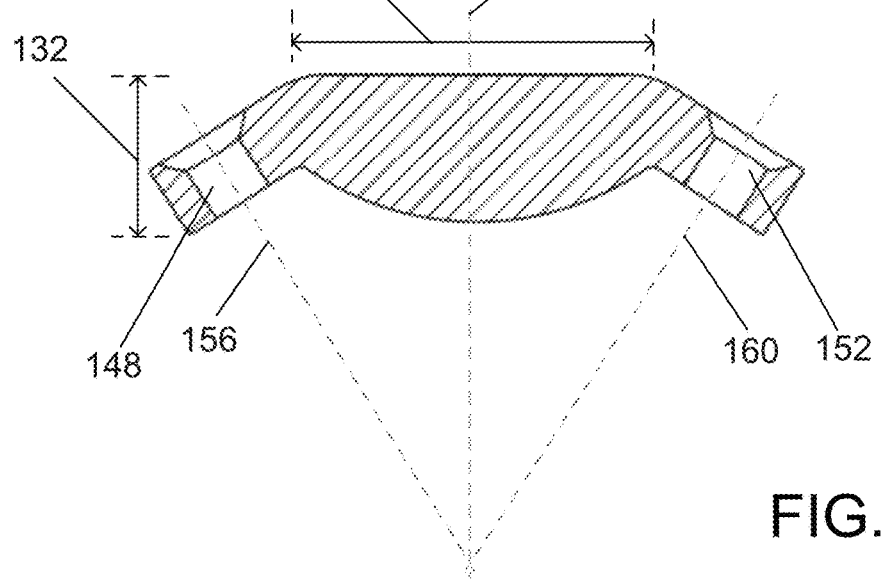
Figure 1D:
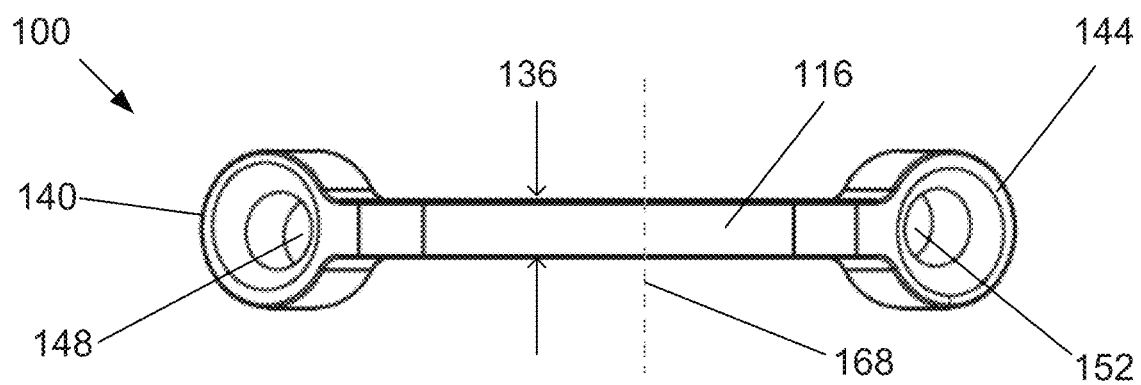
Figure 1E:
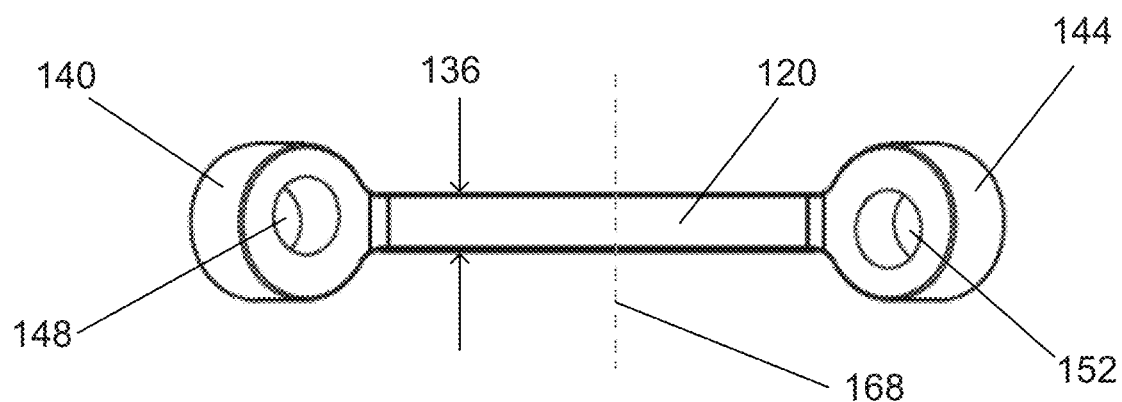
Figure 1F:
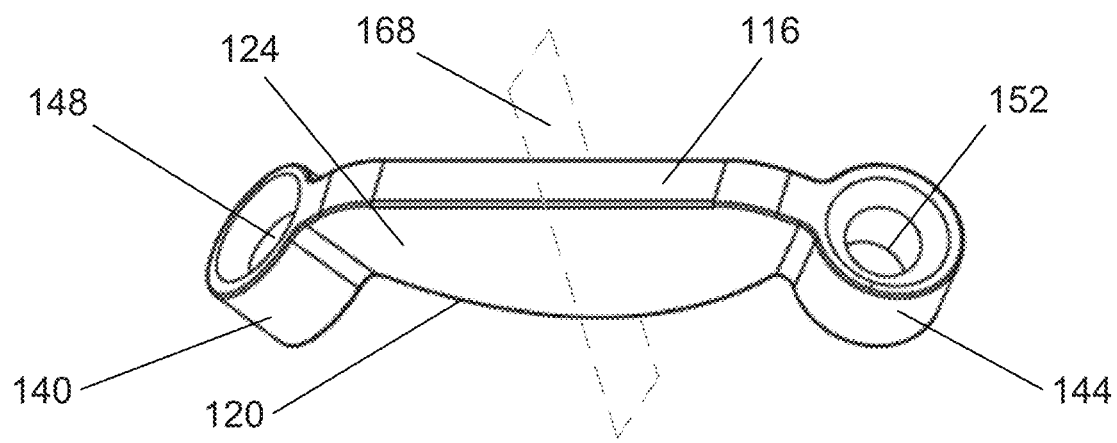

Referring now to the drawings, and more particularly to FIGS. 1A-1F, shown there and designated by the reference numeral 100 are embodiments of the present osteotomy plates. In the embodiments shown, plates 100 have an implant body 104, a first end 108, and an opposing second end 112. In the embodiments shown, body 104 also has an upper edge 116, a lower edge 120, and a pair of opposing sides 124 extending between upper edge 116 and lower edge 120. A length 128 of body 104 is defined as extending between first end 108 and second end 112. A height 132 of body 104 is defined as extending between upper edge 116 and lower edge 120. A width 136 of body 104 is defined as extending between opposing sides 124. In the embodiments shown, body 104 is elongated with length 128 being greater than height 132 and/or width 136. In some embodiments, length 128 is between 10 mm and 40 mm (e.g., 20 mm); height 132 is between 5 mm and 25 mm (e.g., 5 mm); and/or width 136 is between 1 mm and 5 mm (e.g., 2 mm).

In the embodiments shown in FIG. 1A-1F, plates 100 have a first guide member 140 and a second guide member 144. In the embodiments shown, first guide member 140 is coupled to first end 108 and second guide member 144 is coupled to second end 112. In some embodiments, body 104, first guide member 140, and second guide member 144 form a unitary piece. In the embodiments shown, first guide member 140 and second guide member 144 are enlarged relative to body 104. In the embodiments shown, first guide member 140 defines a first fastener hole 148 and second guide member 144 defines a second fastener hole 152. In the embodiments shown, first fastener hole 148 has a central axis 156 and second fastener hole 152 has a central axis 160. First fastener hole 148 and second fastener hole 152 are each configured to receive a fastener 164 (FIG. 5D) coaxial to the respective central axis 156, 160.

In the embodiments shown in FIGS. 1A-1F, upper edge 116 is straight and extends between first guide member 140 and second guide member 144. In some embodiments, upper edge 116 are curved and/or arcuate. In the embodiments shown in FIGS. 1A-1F, lower edge 120 are curved and/or arcuate. In some embodiments, a lateral plane 168 bisects length 128 of body 104. Lateral plane 168 is perpendicular to upper edge 116. In some embodiments, one or more of central axis 156 and central axis 160 extend toward lateral plane 168 and central axis 156 and central axis 160 intersect each other. In some embodiments, central axis 156 and central axis 160 intersect at or on lateral plane 168. In other embodiments, one or more of central axis 156 and central axis 160 extend vertically and are substantially parallel to lateral plane 168. In some embodiments, central axis 156 is substantially parallel to central axis 160. In some embodiments, central axis 156 and/or central axis 160 is configured to be modified from a position where central axis 156 and/or central axis 160 is substantially parallel to lateral plane 168 to a position where central axis 156 and/or central axis 160 extends toward lateral plane 168. In these embodiments, central axis 156 and/or central axis 160 are modified as fastener 164 is secured into a bone.

Figure 2:
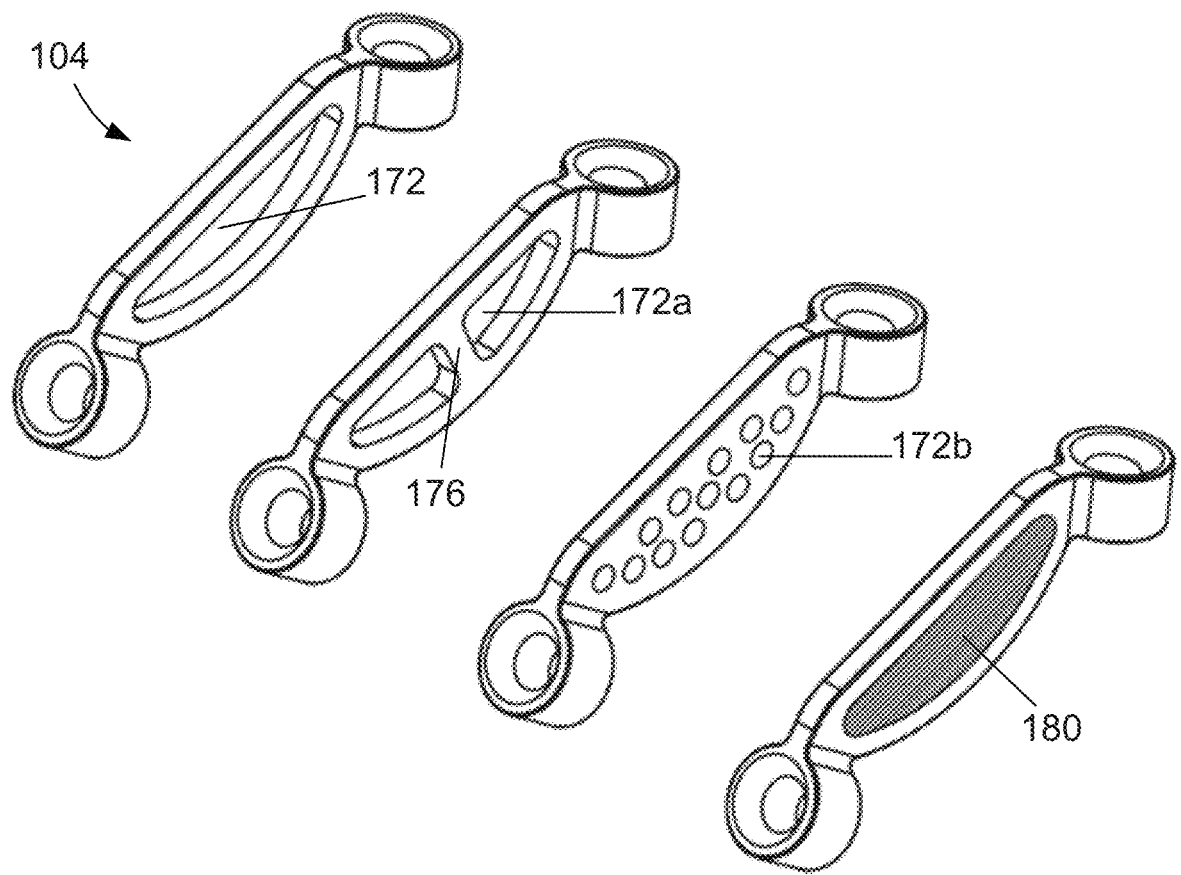
FIG. 2 depicts perspective views of variations of the first embodiment of FIGS. 1A-1F.

In the embodiments shown in FIG. 2, body 104 define one or more holes 172, 172a, 172b that extend between opposing sides 124. In some embodiments, a single hole 172 are elongated with a length of hole 172 being greater than a height and/or width of hole 172. In some embodiments, two holes 172a are each be elongated with a length of each hole 172 being greater than a height and/or width of each hole 172. In this embodiment, two holes 172 are separated by bar 176 that extends between upper edge 116 and lower edge 120. In some embodiments, multiple cylindrical holes 172b extend between opposing sides 124. In some embodiments, body 104 is comprised of a metal. In other embodiments, body 104 is comprised of a plastic. In some embodiments, body 104 is comprised of more than a single type of material or a composite material. In the embodiment shown, body 104 is comprised of a first material and has a filling 180 that is comprised of a second material disposed in one or more of holes 172, 172a, 172b. In some embodiments, body 104 comprises a porous material that may, for example, be osteoconductive and/or osteoinductive. The present implants or plates are configured to extend across and mechanically stabilize a seam or fracture, and a porous exterior surface can resist sliding relative to bone while also encouraging bone growth (e.g. by permitting some circulation or flow to the interface between the implant/plate and the bone. "Osteoconductive" refers to the property/ies of a material and/or surface that serves to promote reparative new bone growth of the native bone. "Osteoinductive" refers to the property/ies of a material and/or surface that encourages undifferentiated osteoprogenitor cells to become active osteoblasts that synthesize bone. A material that is both osteoconductive and osteoinductive will not only serve as a framework for currently existing osteoblasts, but will also trigger the formation of new osteoblasts during the bone repair process. In some embodiments, the porous material may resemble cancellous bone. In some embodiments, at least a portion of the surface of body 104 comprises a porous material (e.g., that is osteoconductive and/or osteoinductive), while an underlying layer of body 104 may comprise a different material. In some embodiments, filling 180 (FIG. 2) comprises porous material while body 104 comprises a different material.

Figure 3A:
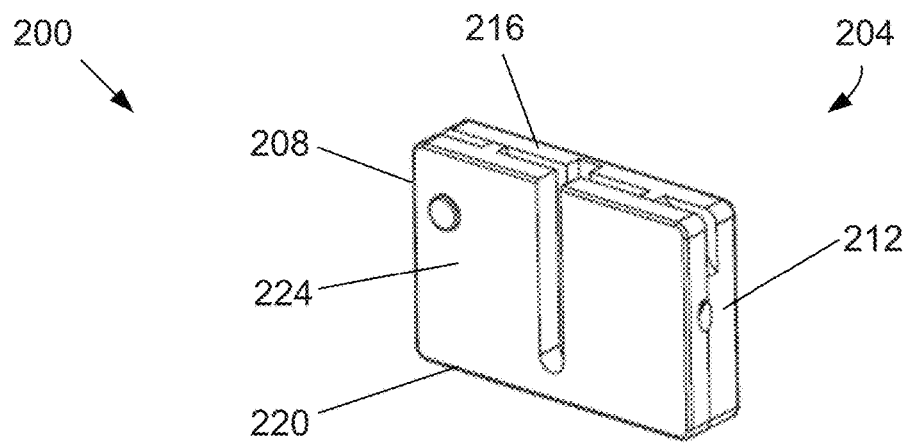
FIGS. 3A-3C depict various views of a first embodiment of the present saw guide configured for use with the osteotomy implant of FIGS. 1A-1F.
Figure 3B:
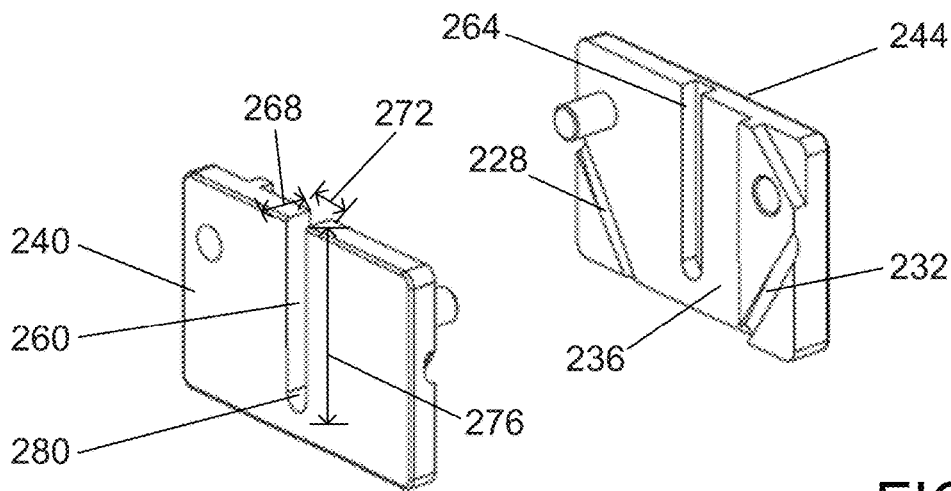
Figure 3C:
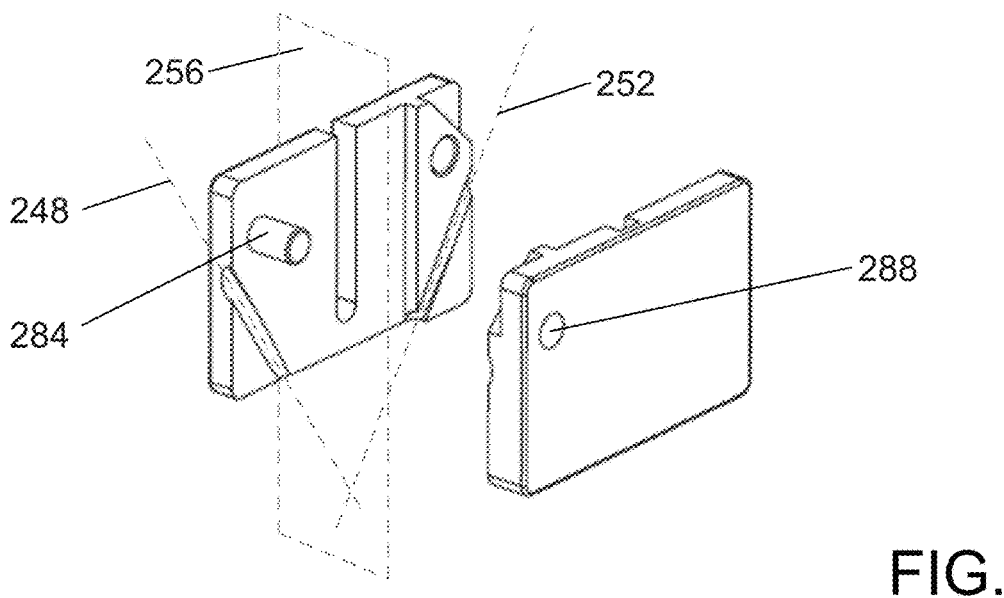

FIGS. 3A-3C depict various views of a first embodiment of the present saw guides configured for use with the osteotomy implant of FIGS. 1A-1F. In the embodiments shown, saw guide 200 has a body 204, a first end 208, and an opposing second end 212. In the embodiments shown, body 204 also has an upper side 216, a lower side 220, and a pair of opposing lateral sides 224 extending between upper side 216 and lower side 220. In the embodiments shown, body 204 comprises a first guide pin channel 228, a second guide pin channel 232, a saw guide channel 236, a first piece 240 and a second piece 244. In some embodiments, body 204 comprises a unitary piece. In the embodiments shown, first piece 240 and second piece 244 are removably coupled to each other and cooperate to form first guide pin channel 228, second guide pin channel 232, and saw guide channel 236 in body 204. In the embodiments shown, a portion of each of first guide pin channel 228, second guide pin channel 232, and saw guide channel 236 is disposed in each of first piece 240 and second piece 244.

In the embodiment shown, first guide pin channel 228 extends between first end 208 and lower side 220 of body 204 and second guide pin channel 232 extends between second end 212 and lower side 220 of body 204. First guide pin channel 228 has a first central axis 248 and second guide pin channel 232 has a second central axis 252. In the embodiment shown, a lateral plane 256 bisects lateral sides 224 of body 204. In this embodiment, lateral plane 256 is perpendicular to upper side 216 and lower side 220. In some embodiments, one or more of first central axis 248 and second central axis 252 extend toward a lateral plane 256 and first central axis 248 and second central axis 252 intersect each other. In some embodiments, first central axis 248 and second central axis 252 intersect at or on lateral plane 256. In some other embodiments, such as those that are used with plates 100c, 100d (FIGS. 8C-8E), one or more of first central axis 248 and second central axis 252 extend vertically between upper side 216 and lower side 220 and are substantially parallel to lateral plane 256. In these embodiments, first central axis 248 is substantially parallel to second central axis 252. In the embodiment shown, saw guide channel 236 extends vertically between and through both upper side 216 and lower side 220. In some embodiments, saw guide channel 236 only extends through lower side 220.

In the embodiments shown, body 204 defines one or more slots 260 in one or both lateral sides 224. For example, in the embodiments shown, a single slot 260 is defined in one of the lateral sides 224. In the embodiment shown, first piece 240 includes a slot 260 and second piece 244 includes a groove 264. In the embodiment shown, a depth 268 of slot 260 extends through one or more lateral sides 224 into saw guide channel 236, as shown by slot 260 of first piece 240. In the embodiment shown, a depth 268 of groove 264 extends from saw guide channel 236 into but not through one or more lateral sides 224, as shown by groove 264 of second piece 244. In the embodiment shown, a width 272 of slot 260 is greater than depth 268 and less than a length 276 of slot 260. In some embodiments, depth 268 is between 1 mm and 5 mm (e.g., 2 mm); width 272 is between 1 mm and 5 mm (e.g., 2 mm); and/or length 276 is between 5 mm and 50 mm (e.g., 10 mm). In the embodiment shown, length 276 of slot 260 extends vertically along one or more lateral sides 224 and extends between upper side 216 to a lower end 280 of slot 260 disposed a predetermined distance above lower side 220. In the embodiments shown, slot 260 is substantially parallel with saw guide channel 236. In the embodiments shown, one or more coupling pins 284 are provided to fit into one or more coupling holes 288 to secure first piece 240 to second piece 244 to form body 204. In the embodiments shown, one or more coupling pins 284 are configured to release from one or more coupling holes 288 to detach first piece 240 to second piece 244. In the embodiments shown, each of coupling pins 284 are unitary with one of first piece 240 and/or second piece 244.

Figure 4:
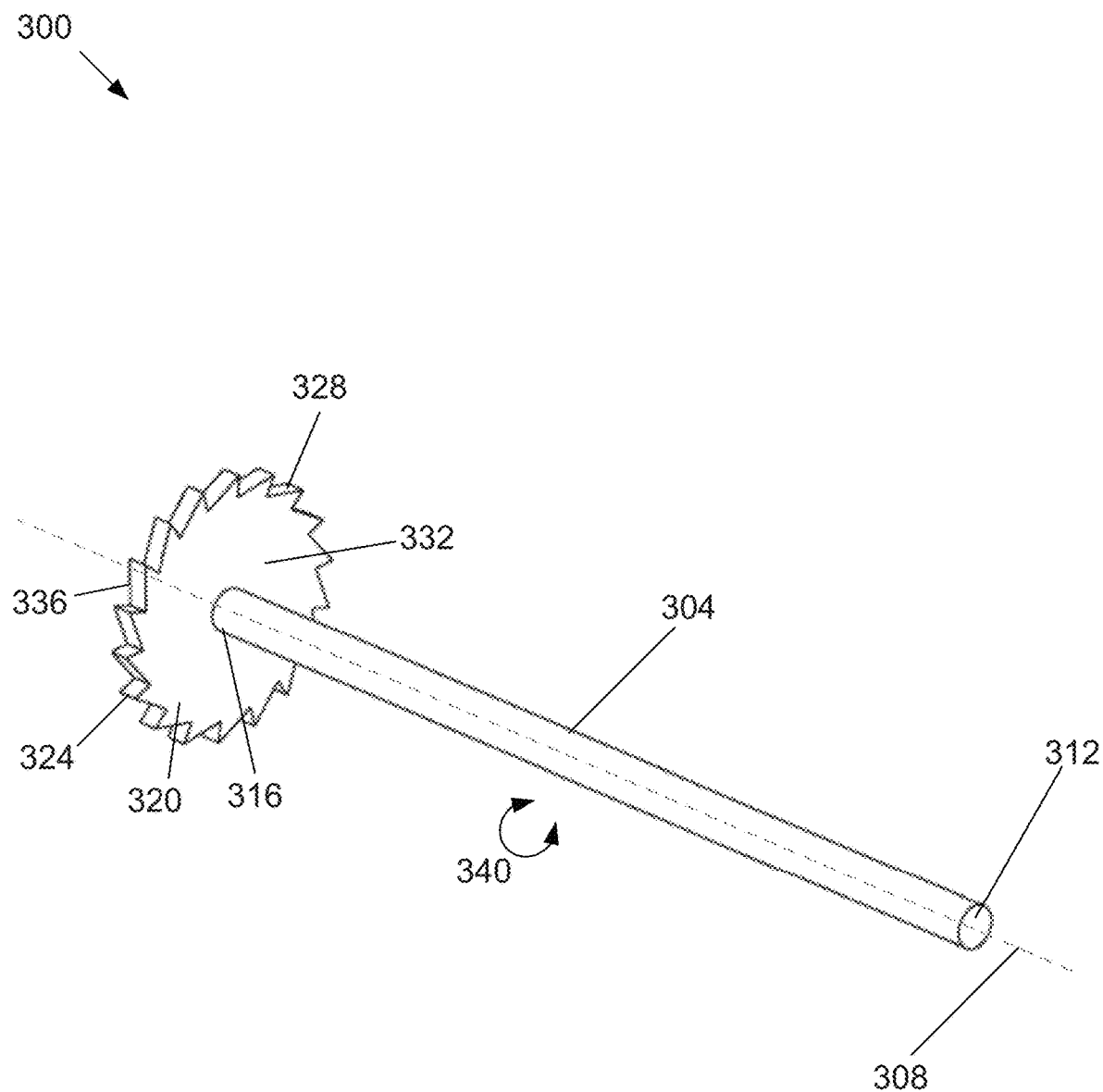
FIG. 4 depicts a perspective view of a first embodiment of a saw blade configured for use with the saw guide of FIGS. 3A-3C.

FIG. 4 depicts a perspective view of a first embodiment of the present saw blade 300 that can be used with saw guide 200. In the embodiment shown, saw blade 300 has a shaft 304 extending outwardly along a rotational axis 308. In the embodiment shown, shaft 304 has a distal end 312 and a proximal end 316. In the embodiment shown, saw blade 300 has a cutting member 320 having an outer perimeter 324 with at least one cutting edge 328 disposed on outer perimeter 324, an upper side 332, and a lower side 336. Saw blade 300 is configured to be rotated around rotational axis 308 (e.g., in direction 340) with cutting edge 328 in contact with a bone to remove a portion of the bone. In some embodiments, the portion of the bone removed is in a shape of outer perimeter 324. In the embodiment shown, outer perimeter 324 is circular. In the embodiment shown, cutting edge 328 comprises one or more serrated cutting teeth configured to remove bone to create a recess in the bone. Other embodiments can include any suitable cutting profile. In the embodiment shown, serrated cutting edge 328 includes one or more notches to reduce backup or collection of bone chips around cutting edge 328 and in the recess created by cutting edge 328. In the embodiment shown, proximal end 316 of shaft 304 is coupled to cutting member 320 at a center of upper side 332. As shown, cutting member 320 is disposed in a plane perpendicular to shaft 304.

Figure 6A:
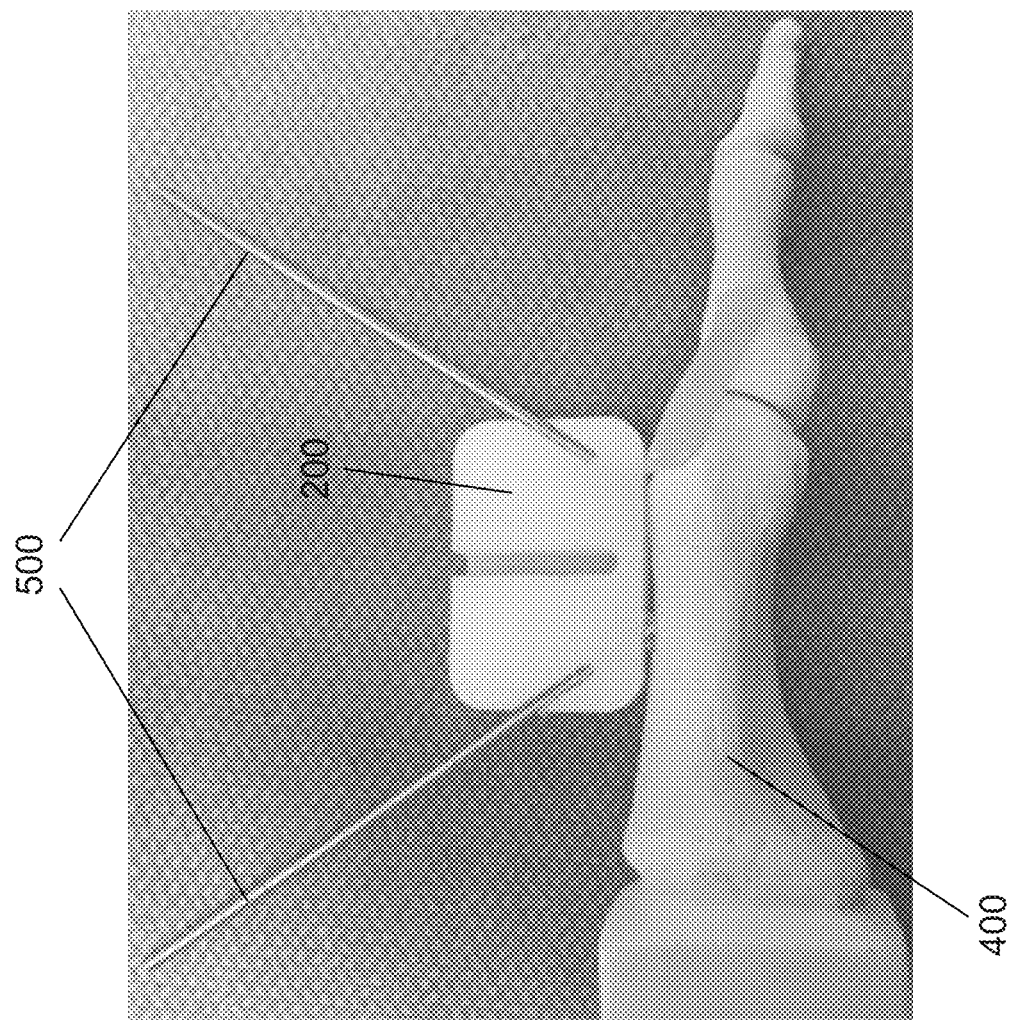
FIGS. 6A-6G depict various views of stages of the present methods using the saw guide of FIGS. 3A-3C with the osteotomy implant of FIGS. 1A-1F.
Figure 6B:
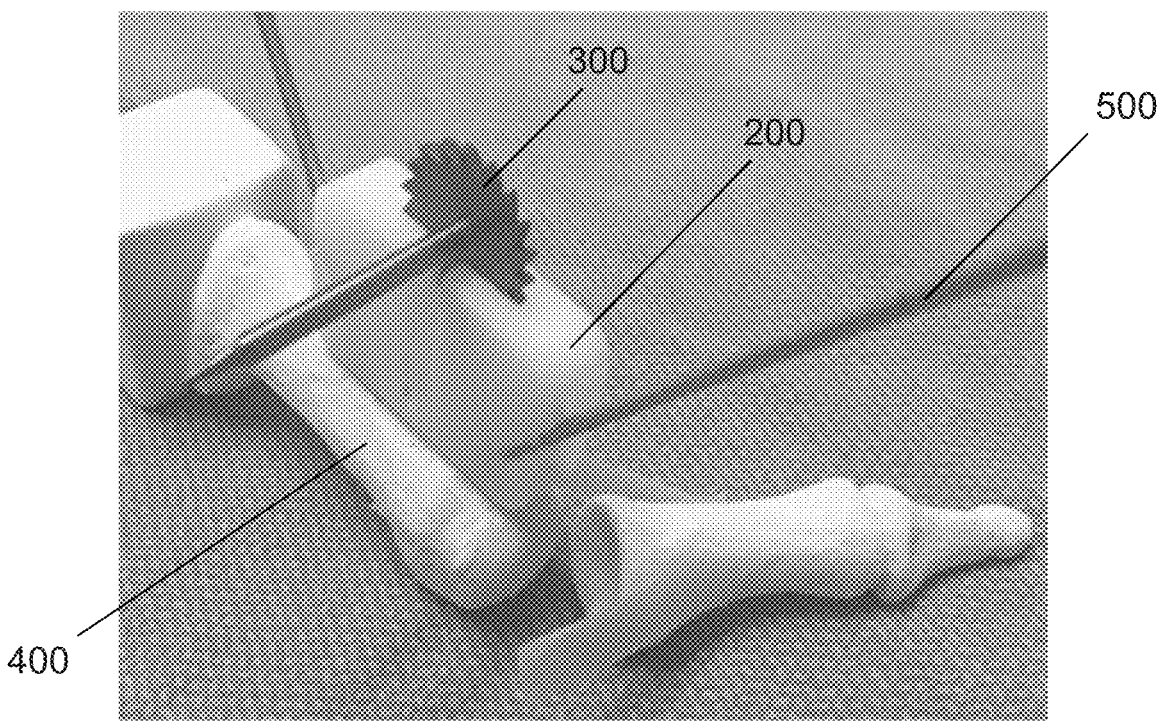
Figure 6C:
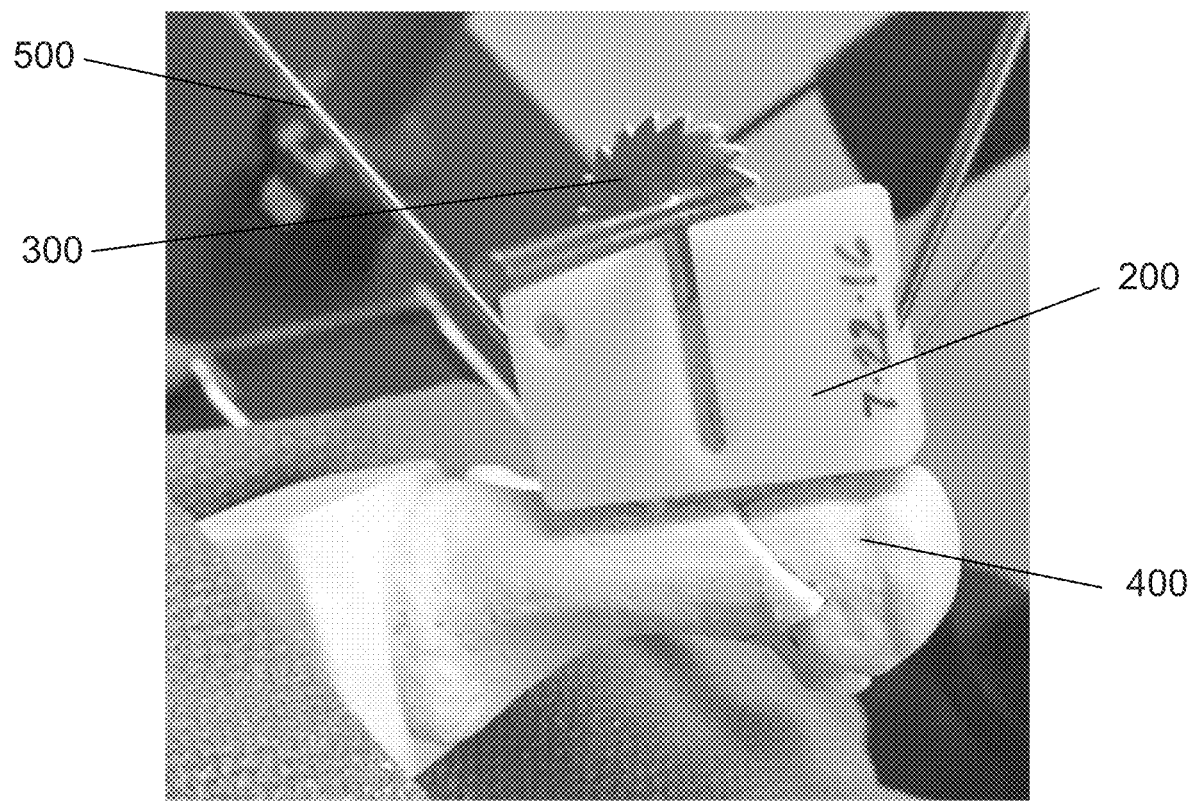
Figure 6D:
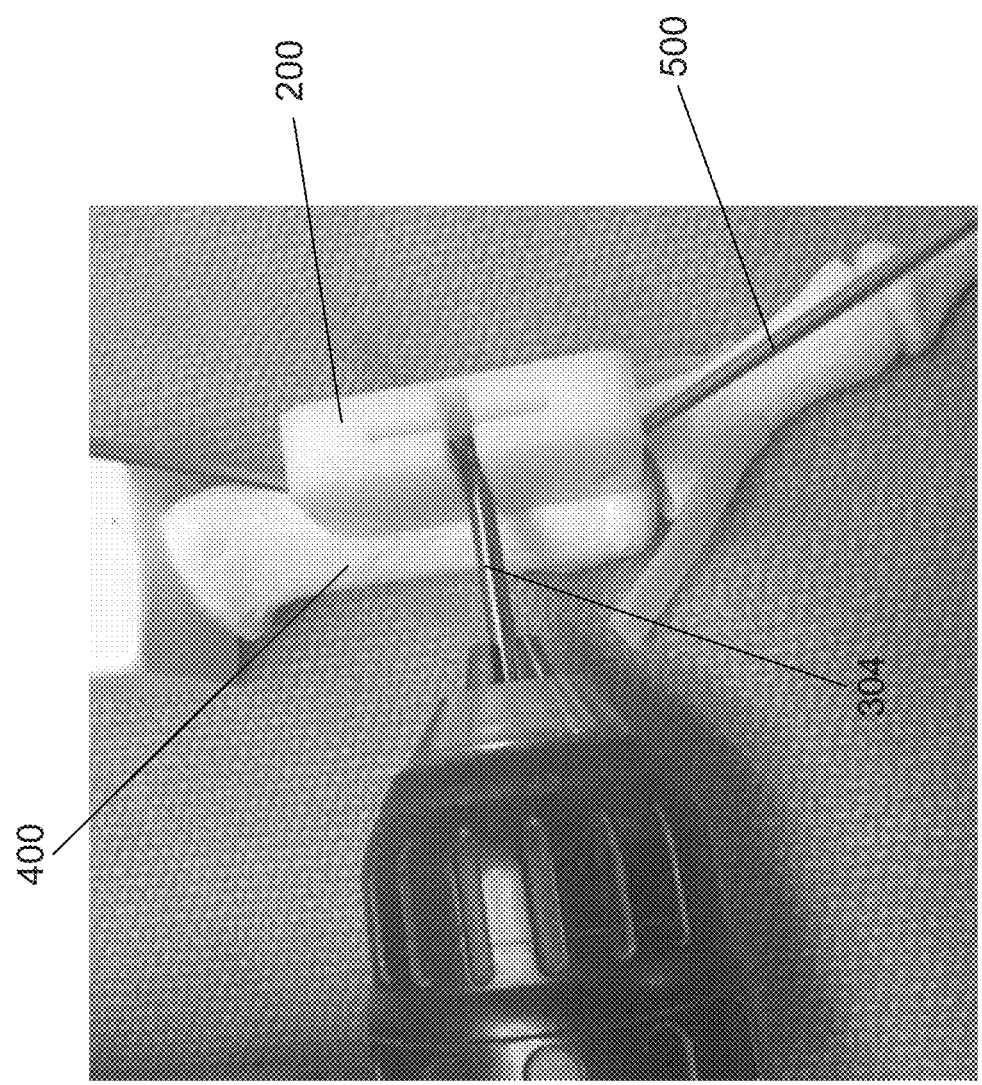
Figure 6E:
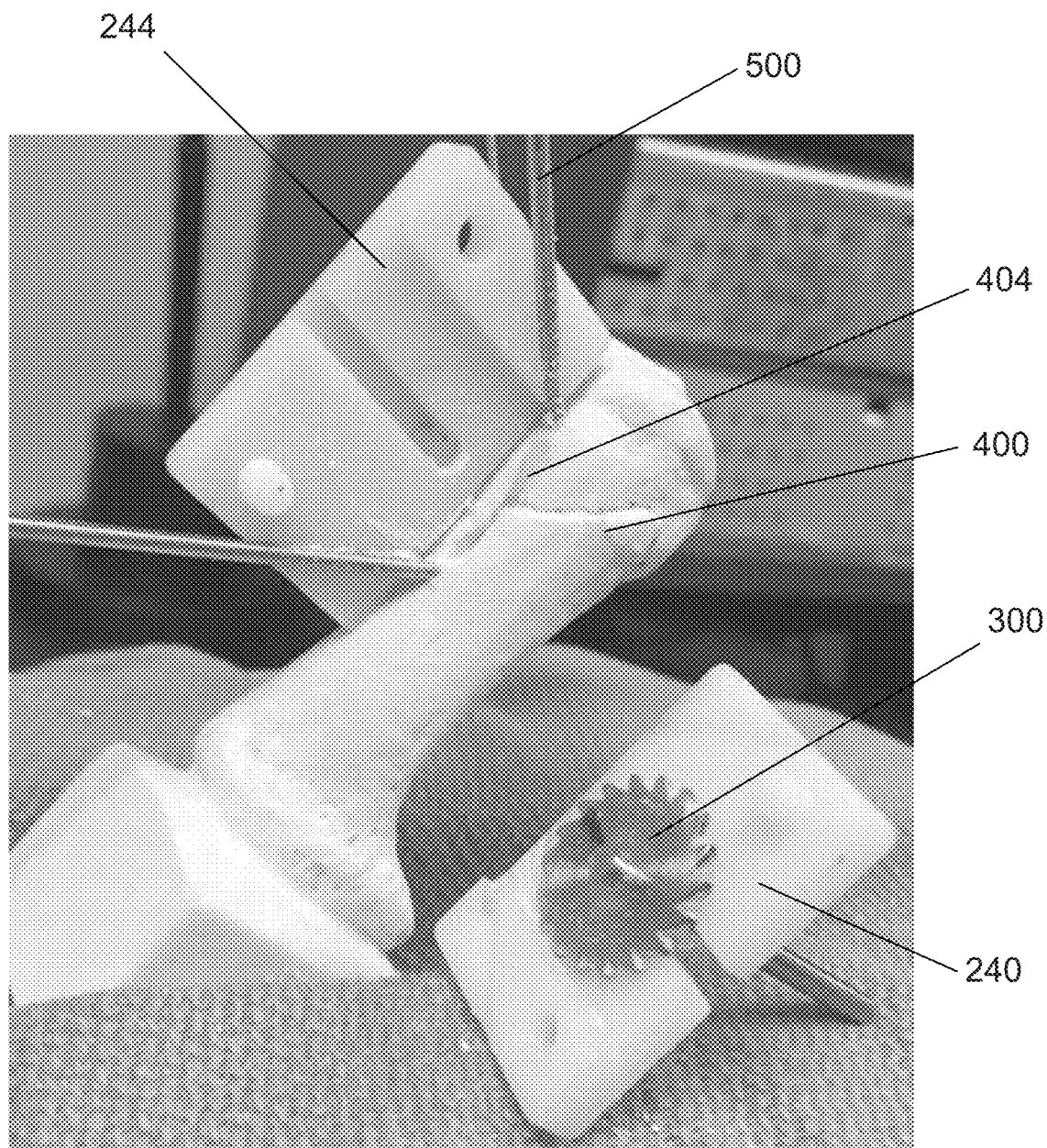

FIGS. 5A-5D and 6A-6G depict various views of stages of the present methods using the saw guide of FIGS. 2A-2C with the osteotomy implant of FIGS. 1A-1F As shown in FIG. 6A, saw guide 200 is positioned to have lower side 220 abut a surface of a bone 400, in which recess 404 and one or more recesses 408 are cut. In the embodiment shown, saw guide 200 is positioned over a single bone. As shown in FIGS. 6C and 6E, saw guide 200 is positioned over two or more bones or sections of bone. Before positioning saw guide 200, saw guide 200 is assembled by coupling first piece 240 to second piece 244.

As shown in FIG. 5A, first piece 240 and second piece 244 are coupled together to form first guide pin channel 228, second guide pin channel 232, and saw guide channel 236 in body 204. In the embodiment shown, a guide pin 500 is inserted into each of first guide pin channel 228 and second guide pin channel 232. In the embodiment shown, first central axis 248 and second central axis 252 intersect at lateral plane 256. When inserted into the guide pin channels 228, 232, guide pins 500 extend along first central axis 248 and second central axis 252, respectively. In the embodiment shown, guide pins 500 are inserted into first guide pin channel 228 at first end 208 and into second guide pin channel 232 at second end 212. In the embodiment shown, guide pins 500 pass through guide pin channels 228, 232, respectively, and extend from body 204 at lower side 220. In the embodiment shown, one or more of first central axis 248 and second central axis 252 extend toward lateral plane 256, and first central axis 248 and second central axis 252 intersect each other (e.g., at or on plane 256). In this way, guide pins 500 are angled in such a way as to have a proximal end 504 of guide pins 400 approach an intersection point. In the embodiment shown, guide pins 500 have a distal end 508 opposite proximal end 504.

Figure 6F:
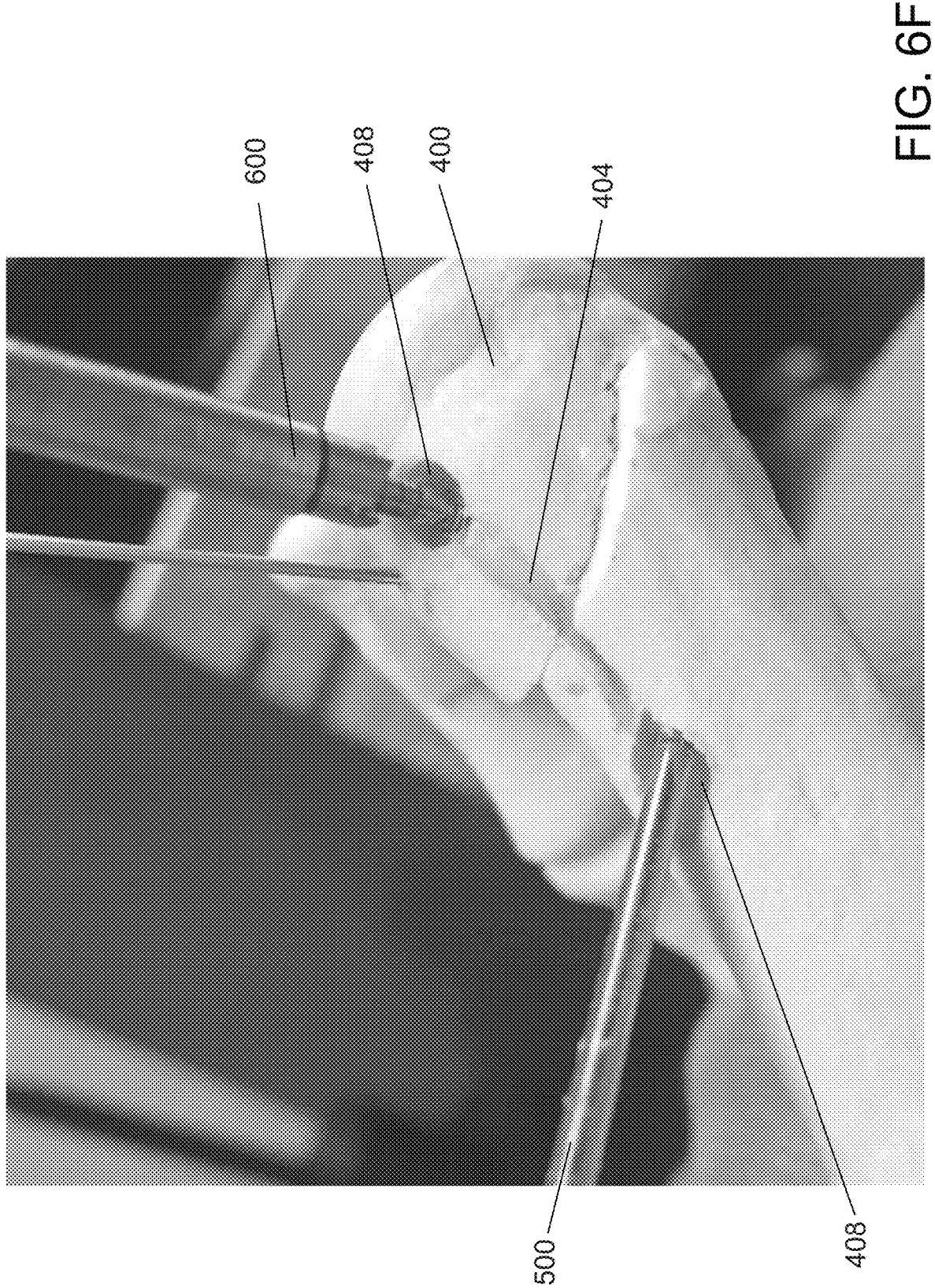

In the embodiment shown, proximal end 504 of guide pins 500 has a tapered tip to enable guide pins 500 to penetrate a bone 400 as shown in FIG. 6A. In some embodiments, guide pins 500 have threads, rough surfaces, and/or some other suitable characteristic near the proximal end 504 to enable guide pins 500 to penetrate a bone and resist removal. In the embodiments shown, guide pins 500 are configured to penetrate the surface of bone 400 to a distance suitable to stabilize guide pins 500 in a position along first central axis 248 and second central axis 252, respectively. As shown in FIGS. 6C, 6E, and 6F, when positioned in this way, each guide pin 500 bridges a cut or break line between two bones or sections of bone 400. Each guide pin 500 can extend from one of the bones or sections of bone 400 into the other bone or section of bone 400. In this way, guide pins 500 stabilizes can stabilize guide 200 and/or stabilize a fracture or injured joint during a bone repair process.

As shown in FIGS. 6B-6C, saw blade 300 is positioned so that cutting edge 328 of cutting member 320 is inserted into saw guide channel 236 at upper side 216 of body 204. In the embodiment shown, shaft 304 extends from saw guide channel 236 through lateral side 224 via slot 260. In some embodiments, cutting member 320 is permanently disposed within saw guide channel 236 so as to preclude insertion and withdrawal of cutting member 320 from saw guide channel 236. In embodiments where shaft 304 is detachable from cutting member 320, shaft 304 is attached to cutting member 320. Cutting member 320 is then moved vertically up and down within saw guide channel 236 as shaft 304 (and thereby cutting member 320) are rotated. In the embodiment shown, shaft 304 moves vertically up and down within slot 260 to control the movement of cutting member 320 within saw guide channel 236. Cutting member 320 is moved within saw guide channel 236 to contact the surface of bone 400. Cutting member 320 contacts the surface of bone 400 by extending out of saw guide channel 236 at lower side 220. In the embodiment shown, lower end 280 of slot 260 is disposed a predetermined distance above lower side 220 of saw guide 200. In the embodiment shown, the predetermined distance between lower end 280 and lower side 220 is sufficient to enable cutting edge 328 to cut a recess 404 into the surface of the bone 400 to a predetermined depth. In the embodiment shown, shaft 304 is moved along slot 260 to contact lower end 280. When shaft 304 is in this position, cutting edge 328 cuts a recess 404 into the bone 400 at a desired depth. Because lower end 280 inhibits the vertical movement of shaft 304, cutting edge 328 is prevented from causing undesired damage to the bone 400 (e.g., by cutting a recess deeper than a desired depth).

As shown in FIG. 6D, shaft 304 is rotated around rotational axis 308. In the embodiment shown, distal end 312 of shaft 304 is coupled to a drill or other mechanized rotation element. In some embodiments, shaft 304 is rotated by hand or by other suitable means. In the embodiment shown, as the shaft 304 rotates, cutting member 320 also rotates around rotational axis 308. As cutting member 320 rotates, cutting edge 328 cuts a recess 404 into the surface of the bone as shaft 304 moves along slot 260. Cutting edge 328 cuts the recess 404 to a depth permitted by the positioning of shaft 304 at lower end 280 of slot 260.

As shown in FIGS. 5B and 6E, saw guide 200 is disassembled after saw blade 300 cuts recess 404 into bone 400. In the embodiments shown, saw guide 200 is disassembled by decoupling first piece 240 from second piece 244. In some embodiments, saw guide 200 is disassembled after saw blade 300 has been withdrawn from saw guide channel 236. In other embodiments, saw guide 200 is disassembled while saw blade 300 is within saw guide channel 232. After saw guide 200 is disassembled and saw blade 300 is removed, guide pins 500 remain embedded in bone 400 in their previous position. In this way, body 204 is removed from guide pins 500 so as to leave guide pins 500 affixed into the bone 400 along first central axis 248 and second central axis 252.

As shown in FIGS. 5C and 6F, a reamer 600 is coupled to (e.g., around) guide pin 500. In the embodiments shown, guide pins 500 remain affixed into a bone in the same position as shown, for example, in FIGS. 5C-5D, after guide 200 is removed. In the embodiments shown, reamer 600 comprises a body 604 that extends outwardly along a rotational axis 608 and body 604 has a distal end 612 and a proximal end 616 with at least one cutting edge 620. Reamer 600 is configured to be rotated around rotational axis 608 (e.g., in direction 624) with proximal end 616 in contact with a bone to remove a portion of the bone (e.g., and impart the shape of cutting edge 620 to the bone).

In some embodiments, cutting edge 620 includes one or more (e.g., two or more, three or more, four or more) cutting edges (e.g., sharpened and/or knife-like edges), an abrasive surface, and/or the like configured to define a particular cutting profile of any suitable shape. For example, in the embodiment shown, cutting edge 620 comprises one or more serrated cutting teeth configured to remove bone to create a recess in the bone. Other embodiments can include any suitable cutting profile (e.g., cutting edges can include any shape that can be rotated around rotational axis 608 to remove bone in the resulting shape). In the embodiment shown, a serrated cutting edge 620 includes one or more recesses to reduce backup or collection of bone chips around cutting edge 620 and in the recess created by cutting edge 620.

In the embodiment shown, reamer 600 further includes an opening 628 at distal end 612 defining a first end of a hollow cavity through which rotational axis 608 extends to permit the reamer to be disposed over a guide pin. A similar opening at proximal end 616 defines a second end of the hollow cavity. Opening 628 is configured such that guide pin 500 can pass through the hollow cavity inside body 604 via opening 628 to permit reamer 600 to be rotated around guide pin 500. For example, in this embodiment, the opening at proximal end 616 receives distal end 508 of guide pin 500 and enables reamer 600 to slide along rotational axis 608 as guide pin 500 moves through the hollow cavity of body 604. In the embodiment shown, rotational axis 608 is the same as first central axis 248 or second central axis 252 of guide pin 500. In this way, reamer 600 moves along guide pin 500 until reamer 600 is disposed with proximal end 616 in contact with bone 400. As shown in FIG. 6F, cutting edge 620 cuts a recess 408 into bone 400 at a point where guide pin 500 is inserted into bone 400 coaxial with rotational axis 608 upon a rotation of reamer 600 around rotational axis 608. In some embodiments, recess 408 is formed at a hole from which guide pin 500 was inserted in bone 400 or removed from bone 400. In the embodiment shown, lip 632 is disposed a predetermined distance from the cutting edge 620. The predetermined distance corresponds to a desired depth of the recess 408. In this way, lip 632 provides a reference point for how deep the cutting edge 620 should cut the recess 408. In the embodiment shown, recess 408 enlarges an end of recess 404. In this way, recess 408 has a sufficient size to receive a guide member 140, 144 of plate 100 into recess 408. In the embodiment shown, reamer 600 is removed from guide pin 500 after the desired recess 408 has been cut. Reamer 600 is then inserted over a second one of the guide pins 500 to repeat the same process described above and cut a recess 408 into the bone 400 at a point where the second guide pin 500 is inserted into bone 400.

Figure 6G:
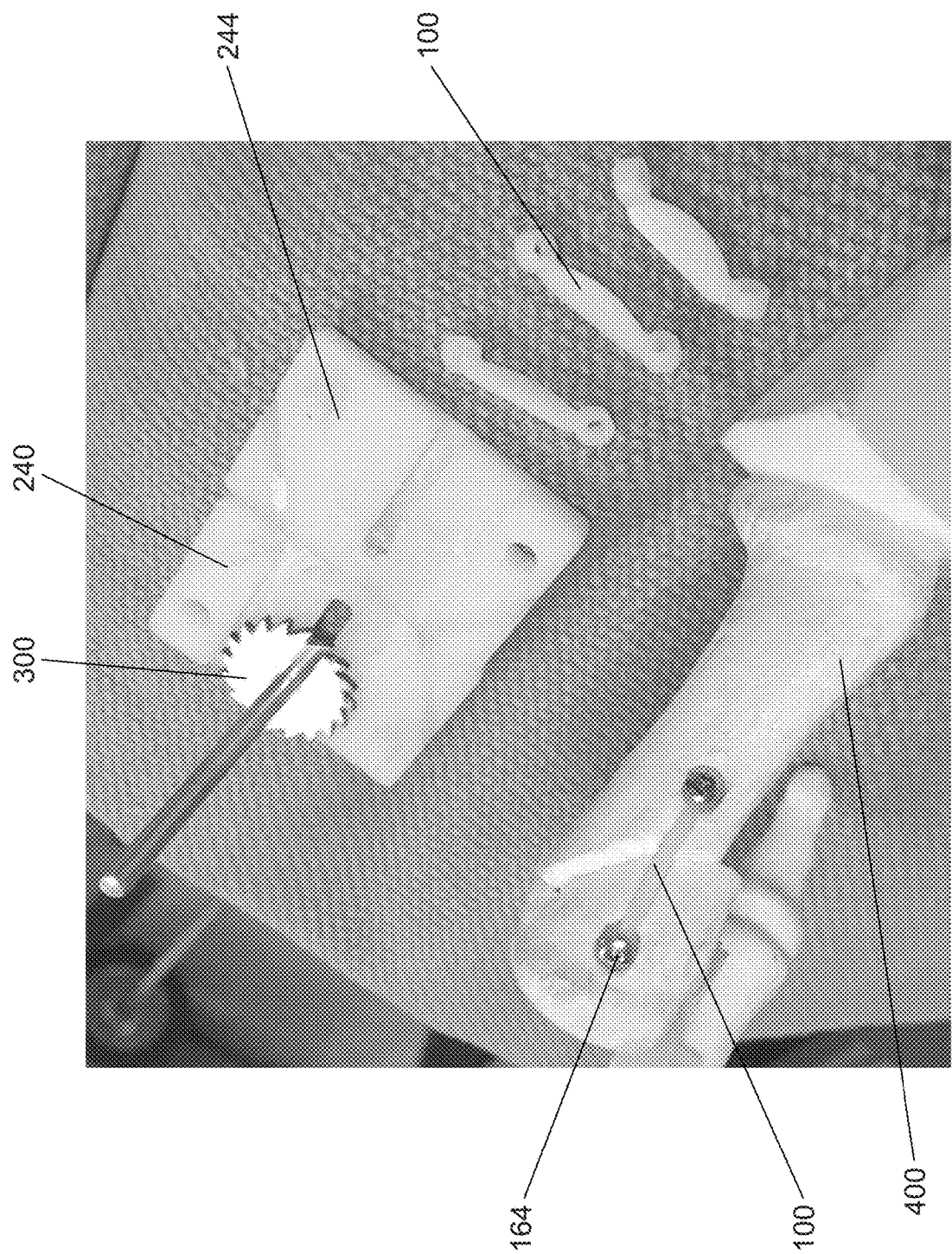

As shown in FIG. 5D, a guide pin 500 is removed while another guide pin 500 remains in a bone 400. In the embodiment shown, first fastener hole 148 of first guide member 140 receives distal end 508 of guide pin 500 and enables plate 100 to slide along central axis 248 of guide pin 500 from distal end 508 toward proximal end 504. Plate 100 slides along central axis 248 of guide pin 500 until it reaches a desired position at bone 400. In other embodiments, both guide pins 500 are removed before positioning the plate or implant. In some embodiments, a desired position of plate 100 is in contact with a surface of the bone 400. In other embodiments, a portion (e.g., first guide member 140) of plate 100 is disposed in a recess 404 cut into the bone 400. As shown in FIG. 6G, plate 100 is positioned into recess 404 and one or more recesses 408 cut into bone 400 by saw blade 300 and reamer 600, respectively. As shown, plate 100 is similar to that shown in FIG. 1A. In some embodiments, plate 100 is positioned in recess 404 and one or more recesses 408 so the entire body 104 is contained within bone 400. In some embodiments, the shape of a bottom surface of recess 404 cut by saw blade 300 is configured to match a shape of lower edge 120 in order to receive body 104 into recess 404. In the embodiment shown, upper edge 116 of body 104 is disposed below a surface of bone 400 so body 104 does not protrude out of bone 400.

As shown in FIG. 5D, second fastener hole 152 of second guide member 144 receives a fastener 164. In the embodiment shown, fastener 164 is received along second central axis 252. In the embodiment shown, fastener 164 is inserted into the recess 408 cut by reamer 600 and secures plate 100 to the bone 400. In some embodiments, recess 408 is formed at a hole from which one of the guide pins 500 was removed. In this same way, the other guide pin 500 is removed and first fastener hole 148 of first guide member 140 receives a fastener 164 along first central axis 248 into a recess 408 cut by reamer 600 to secure plate 100 to the bone 400. As shown in FIG. 6G, when positioned in this way, plate 100 bridges a cut or break line between two bones or sections of bone 400. Each fastener 164 extends from one of the bones or sections of bone 400 into the other bone or section of bone 400. In this way, plate 100 and fasteners 164 stabilize a fracture or injured joint during a healing process.

Figure 7:
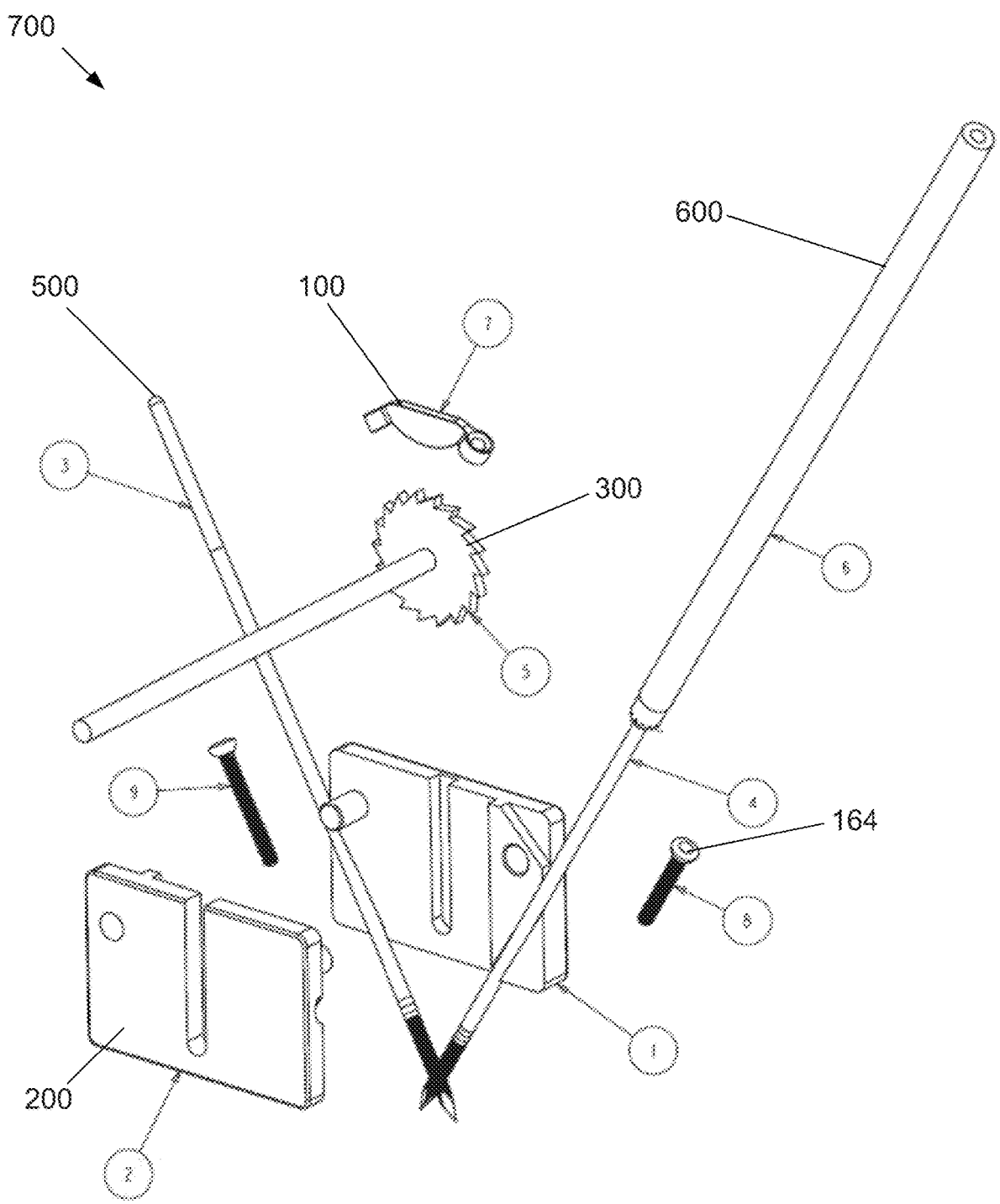
FIG. 7 depicts an exploded view of one of the present kits that includes one or more osteotomy plates of FIGS. 1A-1F; the saw guide of FIGS. 3A-3C; the saw blade of FIG. 4; and two or more guide pins, a reamer, and two or more fasteners as shown in FIGS. 5A-5D.

FIG. 7 depicts an expanded view of an orthopedic device or kit 700 that includes one or more osteotomy plates (e.g., 100), a saw guide (e.g., 200), a saw blade (e.g., 300), one or more guide pins (e.g., 500), a reamer (e.g., 600), and one or more fasteners (e.g., 164).

Figure 8:
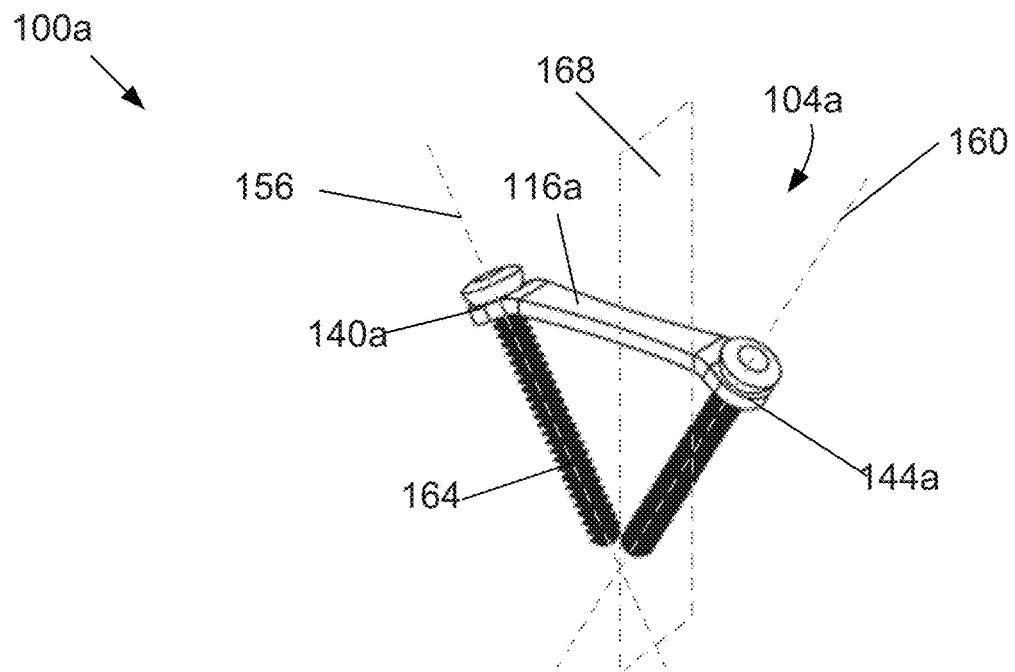
FIG. 8 depicts a perspective view of a second embodiment of the present osteotomy implants.

FIG. 8 depicts a perspective view of a second embodiment of the present osteotomy implants. In this embodiment, lower edge 120a of body 104a is straight and lies parallel to upper edge 116a. In the embodiment shown, width 136 of body 104a is greater than height 136 of body 104a. In the embodiment shown, first fastener hole 148a and second fastener hole 152a are configured to receive a fastener 164 coaxial to the respective central axis 156, 160. In the embodiment shown, central axis 156 and central axis 160 intersect each other. As a result, fasteners 164 are angled toward each other and are configured to affix body 104a to a bone. In embodiments where one or more of central axis 156 and central axis 160 extend vertically and are substantially parallel to lateral plane 168, fasteners 164 modify first guide member 140a and second guide member 144a so that central axis 156 and central axis 160 intersect each other. In these embodiments, central axis 156 and central axis 160 are modified as fasteners 164 are inserted into a bone and affix body 104a to a bone.

Figure 9:
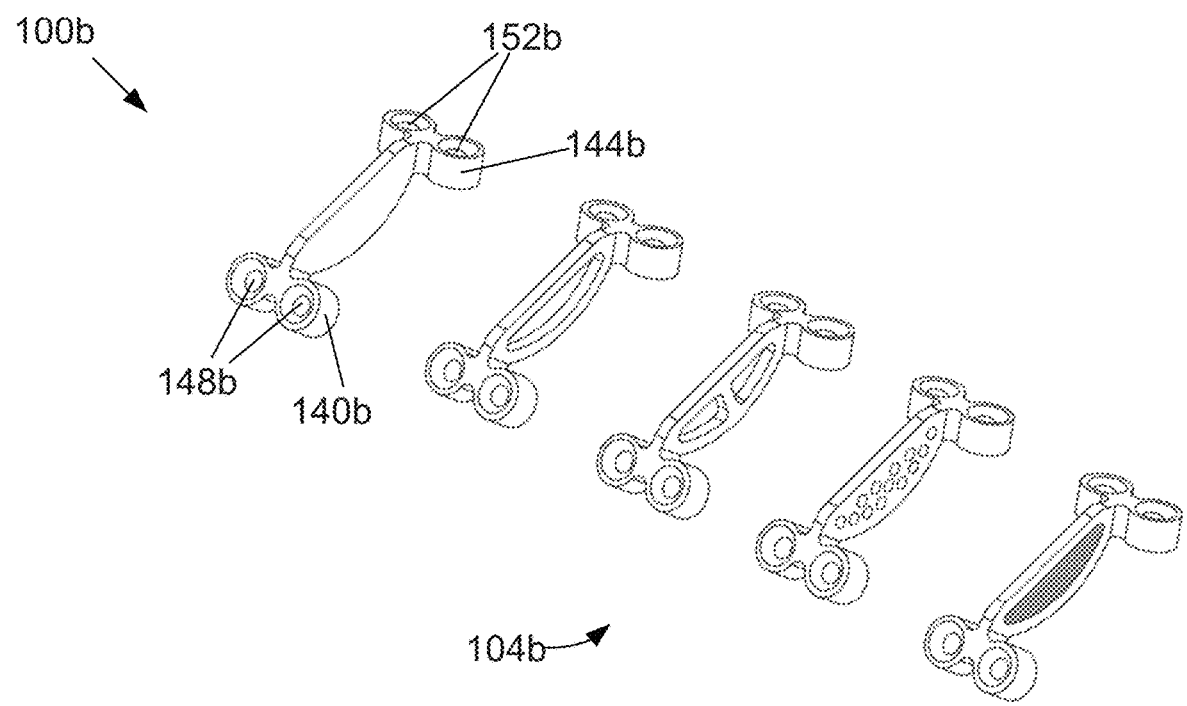
FIG. 9 depicts perspective views of a third embodiment of the present osteotomy implants.
Figure 10A:
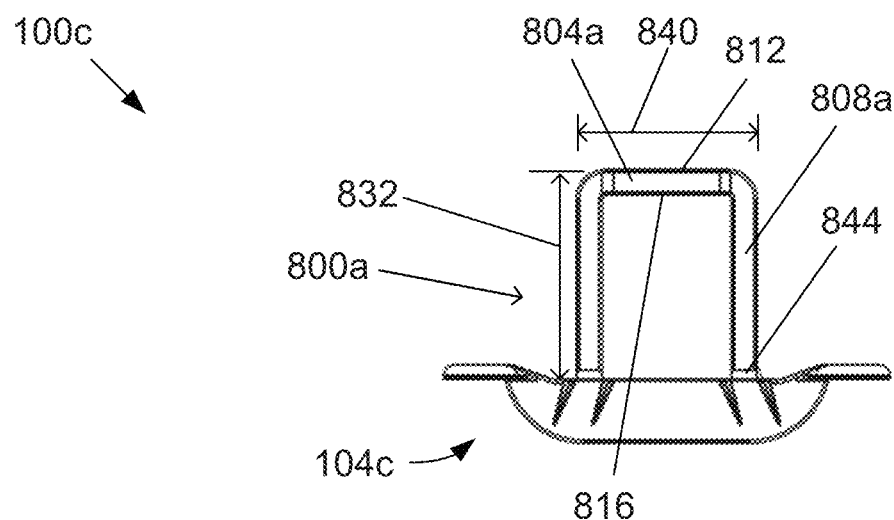
Figure 10B:
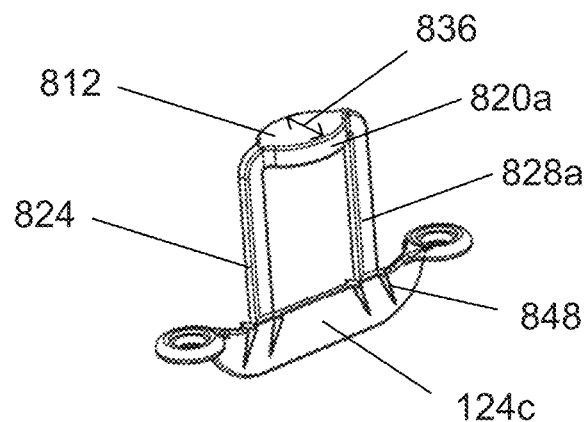
Figure 10C:
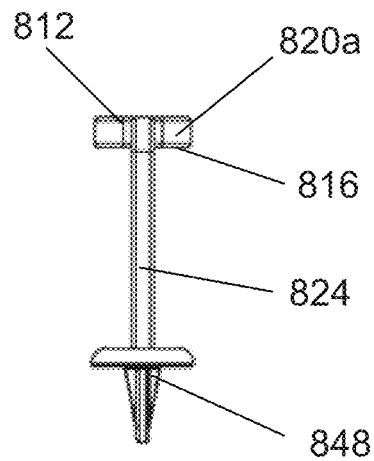
Figure 10G:
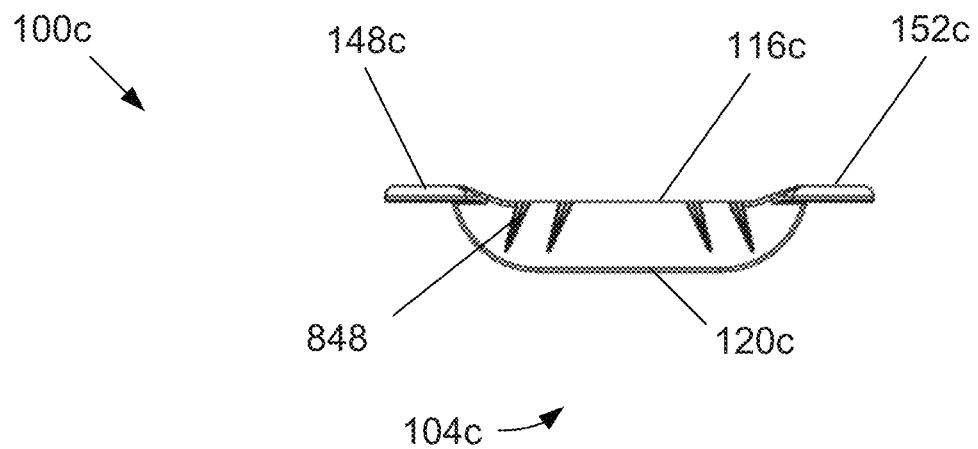
Figure 10H:
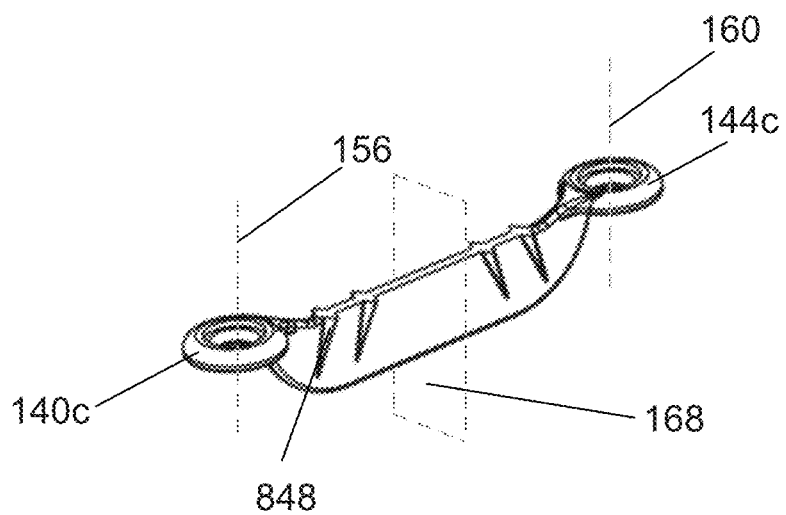
Figure 10I:
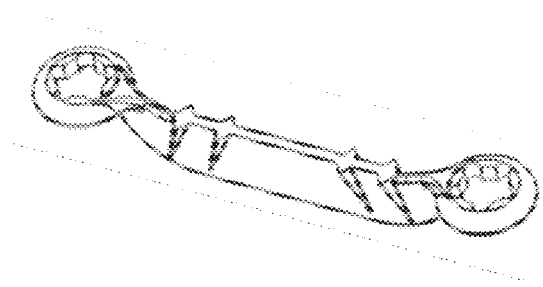
Figure 10J:
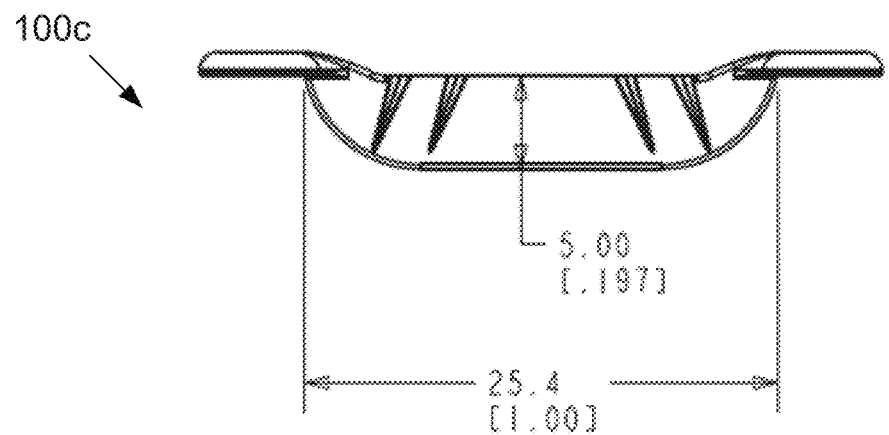
Figure 10K:
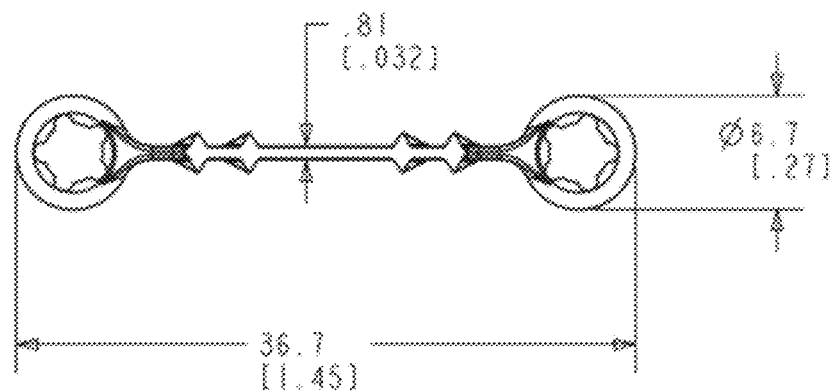
Figure 10L:
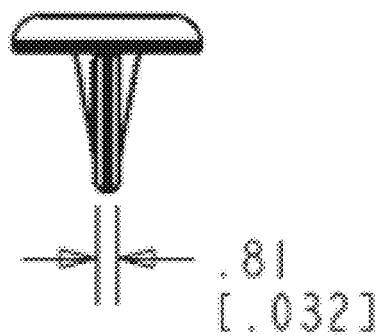
Figure 11A:
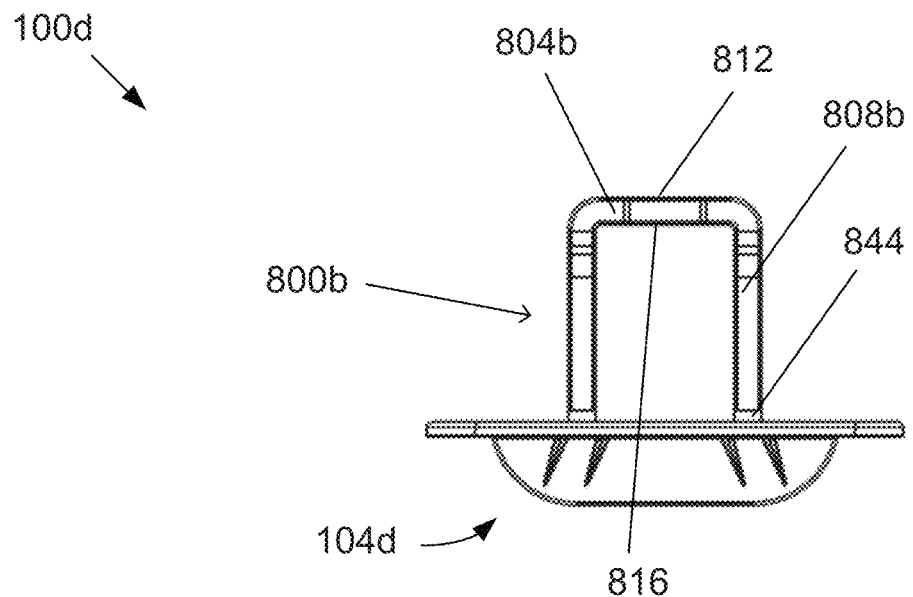
FIGS. 11A-11D depict various views of a fifth embodiment of the present osteotomy implants.
Figure 11B:
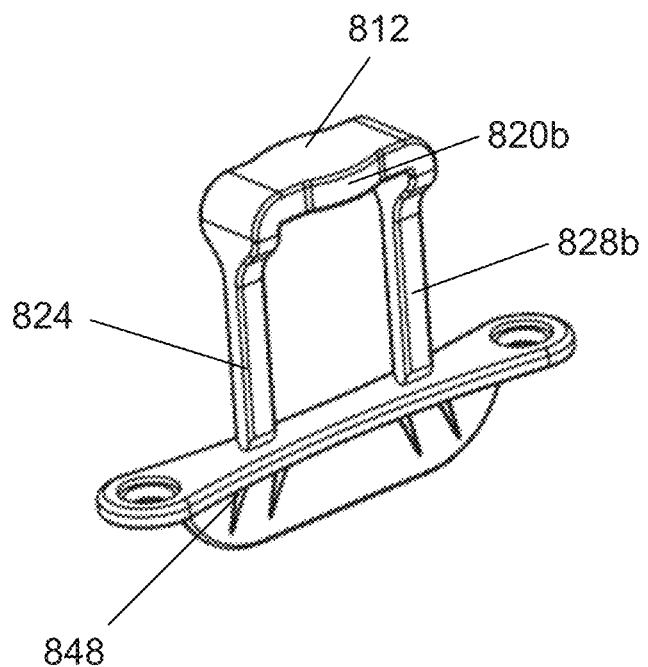
Figure 11C:
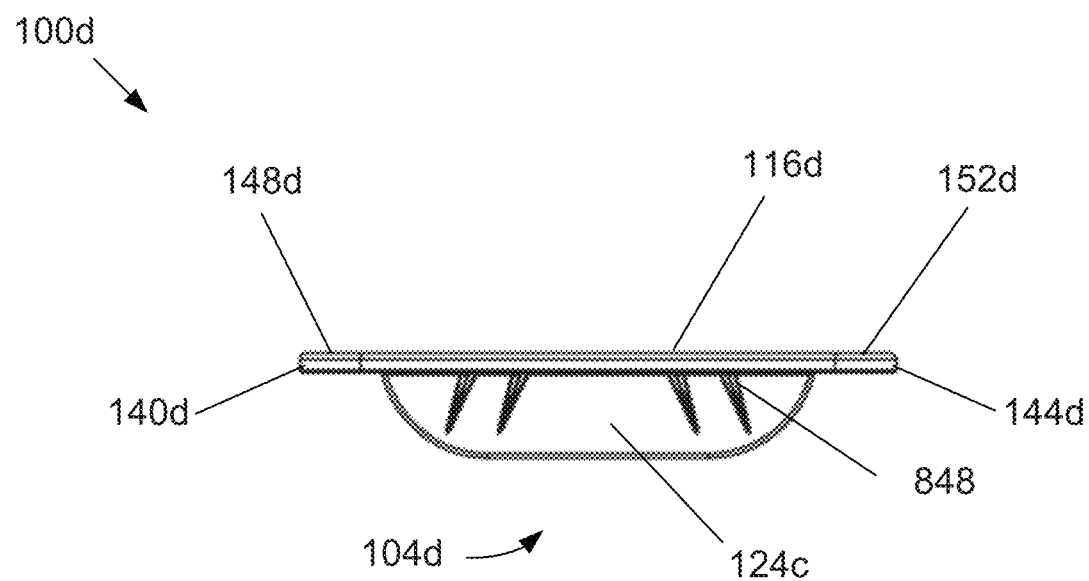
Figure 11D:
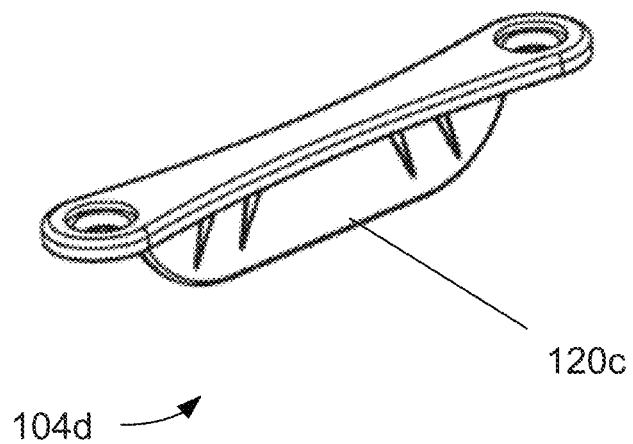

FIG. 9 depicts perspective views of a third embodiment of the present osteotomy implants. In this embodiment, body 104b of plate 100b includes first guide member 140b that has multiple first fastener holes 152b and second guide member 144b that has multiple second fastener holes 152b. In some embodiments, first and second guide members 140b, 144b each have two fastener holes but additional fastener holes can also be used. In some embodiments, one of first and second guide members 140b, 144b has a single fastener hole while the opposite guide member has multiple fastener holes.

FIGS. 10A-10L depict various views of a fourth embodiment of the present osteotomy implants. In the embodiment shown in FIGS. 10A-10L, plate 100c has a handle 800a coupled to body 104c at upper edge 116c. As shown, handle 800a has a cross-member 804a disposed horizontally between upper ends vertical attachment members 808a. In other embodiments, cross-member 804a may be coupled to (e.g., disposed at the upper end of) only one attachment member 808a. In the embodiment shown, cross-member 804a is disposed in a plane parallel to upper edge 116c and attachment members 808a are disposed in a plane perpendicular to upper edge 116*c*. However, cross-member 804*a* and attachment members 808*a* can be disposed in other suitable orientations. In the embodiment shown, cross-member 804*a* has an upper side 812, a lower side 816, and a pair of opposing faces 820*a*. In the embodiment shown in FIGS. 10A-10F, one or more portions of cross-member 804*a* are curved and/or arcuate at opposing faces 820*a*.

In the embodiment shown, each attachment member 808*a* has one or more opposing end faces 824 and one or more opposing lateral faces 828*a*. In the embodiment shown, end faces 824 are straight and parallel to each other, and lateral faces 828*a* are straight and parallel to each other. In other embodiments, one or more portions of end faces 824 and/or lateral faces 828*a* are curved and/or arcuate and/or straight and non-parallel to each other. In the embodiment shown, height 832 of handle 800*a* is greater than width 836 and less than length 840 of handle 800*a*. In some embodiments, height 832 is between 10 mm and 50 mm (e.g., between 15 mm and 20 mm). In some embodiments, width 836 is between 5 mm and 20 mm (e.g., between 5 mm and 8 mm). In some embodiments, length 840 is between 10 mm and 60 mm (e.g., between 10 and 20 mm). FIGS. 10D-10F and 10J-10L also include dimensions (in inches) for at least one exemplary configuration of embodiment 10*c*.

In the embodiment shown, one or more detachable joints 844 are disposed between attachment members 808*a* and body 104*c*. As shown, detachable joints 844 are disposed at a lower end of attachment members 808*a* and at upper edge 116*c* of body 104*c*. Detachable joints 844 detacheably couple handle 800*a* to body 104*c*. In the embodiment shown, detachable joints 844 are configured to enable a separation of handle 800*a* from body 104*c* by bending handle 800*a* relative to body 104*c* to cause joints 844 to break and permit the handle to be removed from the body without damage to the body. Body 104*c* is shown in FIGS. 10A-10F before handle 800*a* has been separated from body 104*c* with detachable joints 844 intact, and is shown in FIGS. 10G-10L after handle 800*a* has been separated from body 104*c* via detachable joints 844. In some embodiments, handle 800*a* is used to position body 104*c* into a certain desired position and/or configuration and then separated from body 104*c* after body 104*c* has been positioned into the desired position and/or configuration. In the embodiment shown, central axis 156 and central axis 160 of fastener holes 148*c*, and 152*c*, respectively, extend vertically and are be substantially parallel to lateral plane 168. However, in other embodiments, central axis 156 and central axis 160 are configured to intersect each other as described previously.

In the embodiment shown, one or more barbs 848 are disposed on opposing sides 124*c* of body 104*c*. As shown, barbs 848 extend along opposing sides 124*c* from upper edge 116*c* toward lower edge 120*c*. In this embodiment, each barb 848 is tapered such that a width of the barb is greater at upper edge 116*c* and decreases as the barb extends toward lower edge 120*c* (with the width of each barb 848 being measured in the same plane as the width 136 of body 104). In the embodiment shown, each barb 848 extends at an angle away from lateral plane 168 such that a distance between the barb 848 and lateral plane 168 (and between a pair of barbs on opposing sides of plane 168) increases along the length of each barb 848 approaching lower edge 120*c*. In the embodiment shown, barbs 848 engage the bone on either side of a slot into which body 104 is inserted to draw opposing portions of the bone together along the length of body 104*c*, and thereby provide compression of the portions of bones into each other. In this way, barbs 848 can compress bone portions or pieces on opposing sides of a seam or break, and thereby provide compression across the seam or break, to stabilize the seam or fracture.

As shown in FIGS. 10A-10L, and similar in some respects to others of the present bone-implant apparatuses (e.g., 100, 100*b*, 100*d*, 100*e*), bone implant apparatus 100*c* includes an a lower portion (e.g., a majority) of implant body 104*c* extends below at least a portion (e.g., all, as shown) of the lower bone-facing surface of first guide member 140*c* and/or below at least a portion of the lower bone-facing surface of second guide member 144*c*. For example, in the depicted embodiment, a majority of implant body 104*c* extends below the lower bone-facing surfaces of both of guide members 140*c* and 144*c*. In this configuration, and as described in more detail below, implant body 104*c* can extend into a slot that is cut into and across a seam between first and second bone portions while fasteners (e.g., screws) extend through fastener holes 148*c* and 152 into the respective first and second bone portions. In this way, the fasteners can secure the implant to the bone to resist vertical movement of the implant relative to the bone portions and to resist horizontal separation of the bone portions, while the elongated body member 104 resists rotation and lateral movement of the bone portions relative to each other. In this way, implant 100*c* is configured to (1) resist relative movement between the bone segments, and (2) distribute forces on the implant over a relatively larger surface area to reduce maximum point loads and stresses on the bone portions and the implant, both in a way and to a greater degree than is possible with prior art implants.

FIGS. 11A-11D depict various views of a fifth embodiment 100*d* of the present osteotomy implants. Implant or plate 100*d* is substantially similar to implant 100*c* and, for brevity, the differences are therefore primarily described here rather than repeating every similar feature. For example, plate 100*d* comprises body 104*d* and handle 800*b*. However, upper edge 116*d* of body 104*d* has a width greater than a width of upper edge 116*c* and greater than a width lower edge 120*c*. In the embodiment shown, upper edge 116*d* includes a widened (relative to the majority of body 104*d*, as shown) portion that is aligned (and substantially co-planar) with first guide member 140*d* and second guide member 144*d*. Implant 100*d* also differs relative to implant 100*c* in that outer portions of cross-member 804*b* of handle 800*b* are straight at opposing faces 820*b*, while central portions of cross-member 804*b* are curved and/or arcuate at opposing faces 820*b*. In the embodiment shown, lateral faces 828*b* of attachment members 808*b* are tapered such that the width of lateral faces 828*b* increases to the width of cross-member 804*b* where lateral faces 828*b* meet opposing faces 820*b*.

Figure 12A:
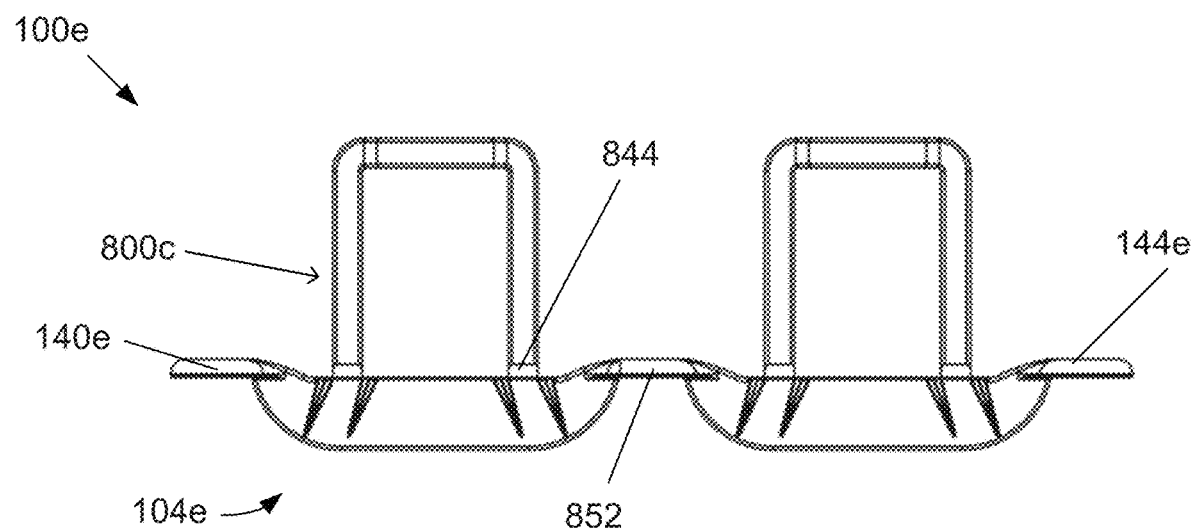
FIGS. 12A-12F depict various views of a sixth embodiment of the present osteotomy implants.
Figure 12B:
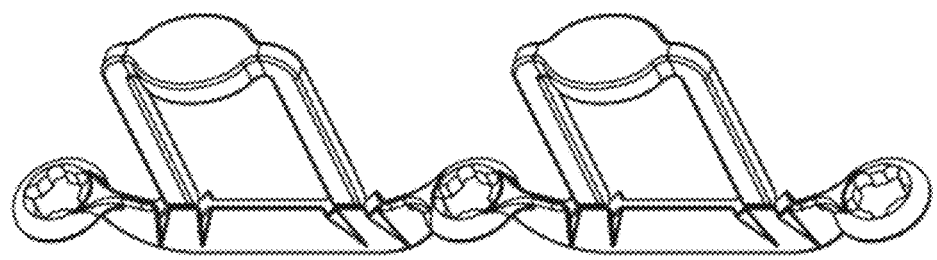
Figure 12C:
Figure 12D:
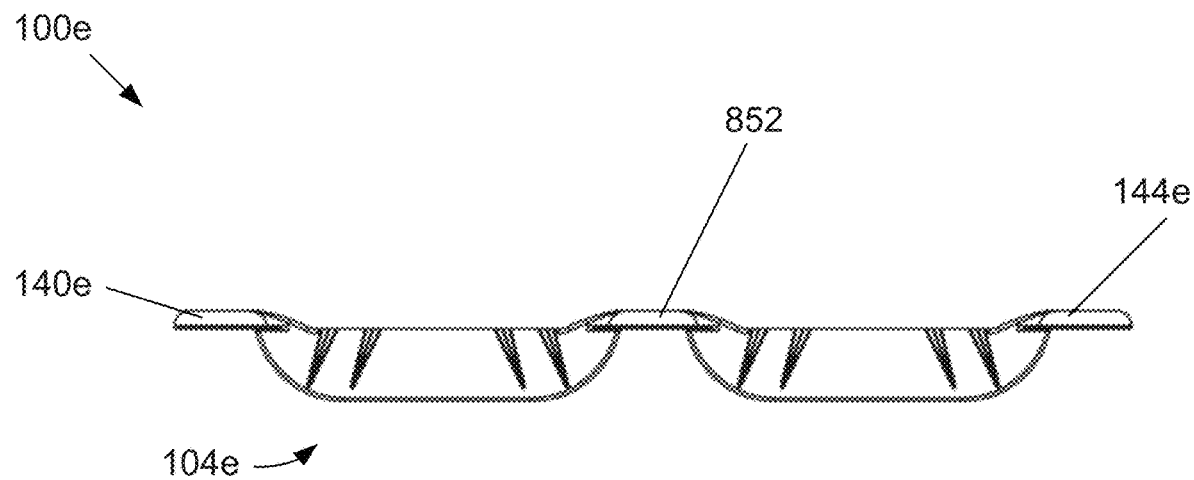
Figure 12E:
Figure 12F:

FIGS. 12A-12F depict various views of a sixth embodiment 100*e* of the present osteotomy implants. Implant 100*e* is substantially similar to implant 100*c* and, for brevity, the differences are therefore primarily described here rather than repeating every similar feature. In the embodiment shown, plate 100*e* comprises multiple bodies 104*e* extending along the same plane as a length 128 of the bodies 104*e*. In the embodiment shown, bodies 104*e* are substantially similar to bodies 104*c* or 104*d* discussed previously except that bodies 104*e* share a common guide member 852 disposed between bodies 104*e* and that couples bodies 104*e* to each other. Common guide member 852 is substantially similar to first and second guide bodies 140*e*, 144*e* except common guide body 852 is coupled to two bodies 104*e* instead of one. Although the embodiment shown has two bodies 104*e*, additional bodies may be used. Similar to bodies 104*c*, 104*d* discussed previously, each body 104*e* has a handle 800*c* attached to body 104e via detachable joints 844c. Bodies 104e are shown in FIGS. 12A-12C before handles 800c have been separated from bodies 104e with detachable joints 844 intact, and in FIGS. 12D-12F after handles 800c have been separated from bodies 104e via detachable joints 844. The embodiments shown in FIGS. 12A-12F may be useful when multiple break lines or fractures are present.

Figure 13:
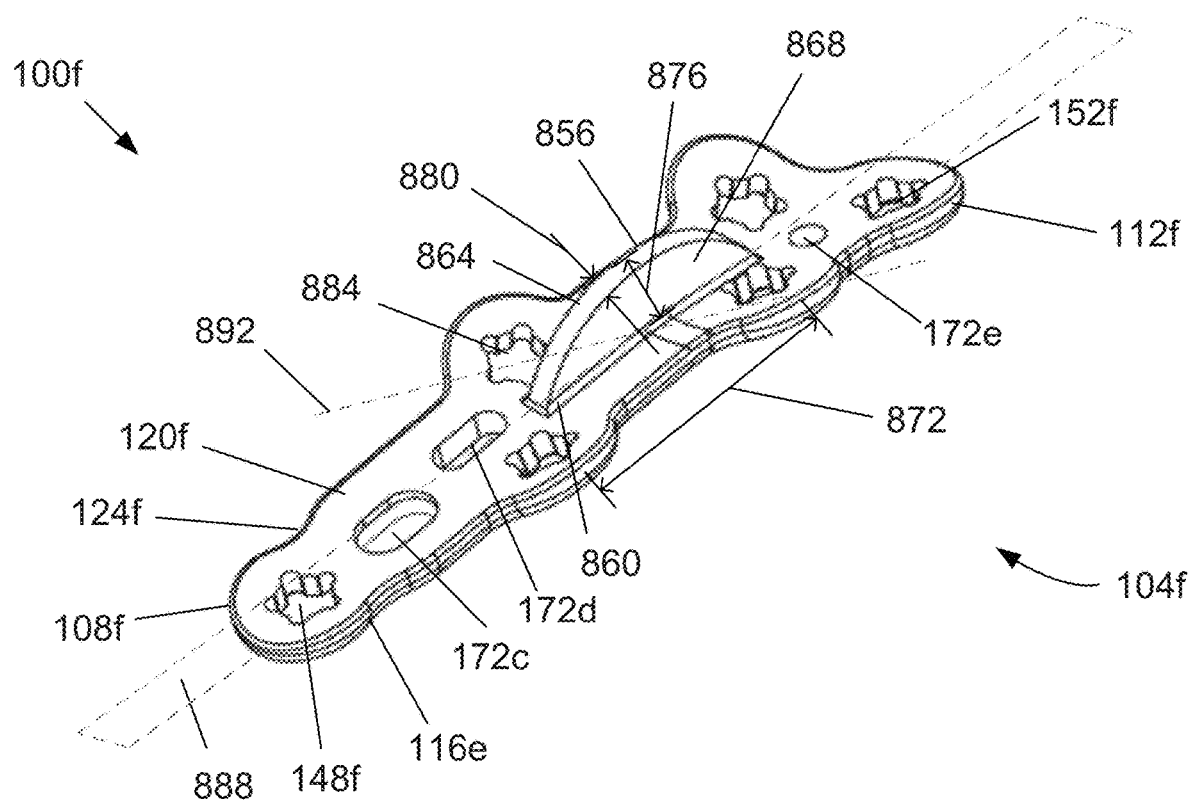
FIG. 13 depicts a perspective view of a seventh embodiment of the present osteotomy implants.

FIG. 13 depicts a perspective view of a seventh embodiment of the present osteotomy implants. In the embodiment shown in FIG. 13, body 104f comprises a protrusion 856. Protrusion 856 has an upper edge 860, a lower edge 864, and a pair of opposing sides 868 extending between upper edge 860 and lower edge 864. In the embodiment shown, upper edge 860 is straight and directly abuts lower edge 120f of body 104f In the embodiment shown, protrusion 856 is elongated with length 872 being greater than height 876 and/or width 880. In the embodiment shown, length 128 of body 104f is greater than length 872 of protrusion 856, height 132 of body 104f is less than height 876 of protrusion 856, and width 136 of body 104f is greater than width 880 of protrusion 856. In the embodiment shown, lower edge 864 of protrusion 856 is curved and/or arcuate. In the embodiment shown, upper edge 116e is convex between opposing sides 124f and lower edge 120f of body 104f is concave between opposing sides 124f While a first fastener hole 148f is disposed at first end 108f and a second fastener hole 152f is disposed at second end 112f, additional fastener holes 884 are disposed in body 104f that extends between upper edge 116f and lower edge 120f In some embodiments, a coronal or frontal plane 888 bisects width 136 of body 104f. In the embodiment shown, one or more additional fastener holes 884 have a central axis 892 that extends toward coronal plane 888. In some embodiments, central axis 892 extends vertically and substantially parallel to coronal plane 888.

In the embodiment shown in FIG. 13, body 104f defines one or more holes 172c, 172d, 172e, that extend between upper edge 116f and lower edge 120f. In some embodiments, one or more holes 172c, 172d, 172e are elongated with a length of hole 172c, 172d, 172e being greater than a height and/or width of hole 172c, 172d, 172e. In some embodiments, one or more holes 172c, 172d, 172e have a width of hole 172c, 172d, 172e being greater than a height and/or length of hole 172c, 172d, 172e. In some embodiments, one or more cylindrical holes 172e extend between upper edge 116f and lower edge 120f. In some embodiments, lower edge 120f of body 104f is concave to conform to a convex bone surface. Fasteners 164 are used to affix body 104f to a bone 400 via one or more fastener holes 148f, 152f, 884. In some embodiments, one or more guide pins 400 pass through one or more fastener holes 148f, 152f, 884 and/or one or more holes 172c, 172d, 172e. Protrusion 856 is configured to be received into a recess 404 cut into a bone 400. In some embodiments, the recess 404 is the same shape as protrusion 856 so as to receive lower edge 864 into the recess 404 to abut a lower surface of the recess 404.

Figure 14A:
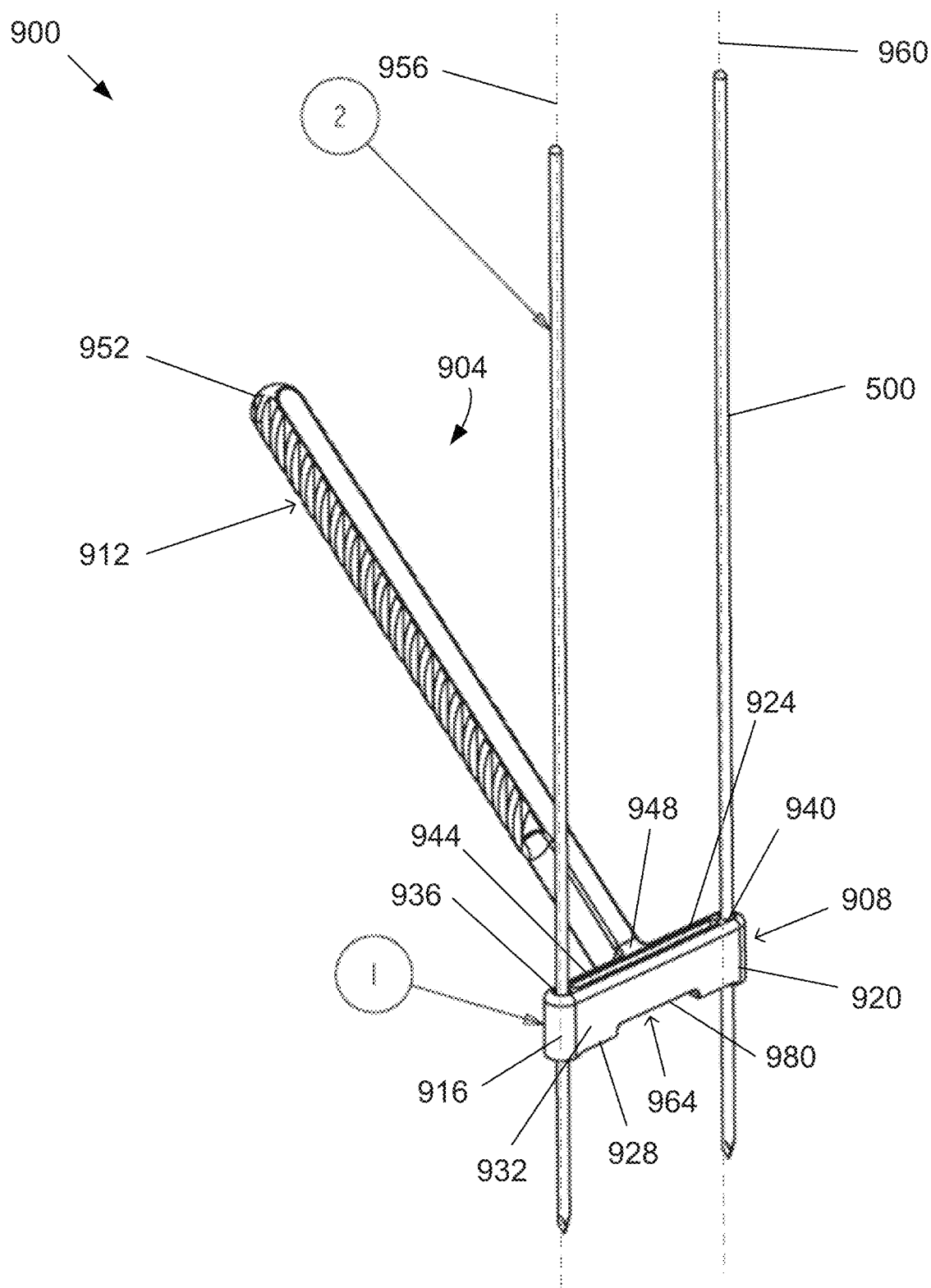
FIGS. 14A-14G depict a second embodiment of the present saw guide and various views of stages of the present methods using the second embodiment of the saw guide with the osteotomy implant of FIGS. 10A-10L.

FIG. 14A depicts a perspective view of a second embodiment of the present saw guides 900 configured for use with the osteotomy implant of FIGS. 10A-10L. In the embodiment shown, saw guide 900 has a body 904 comprising a guide head 908 and a handle 912. In the embodiment shown, guide head 908 is unitary with handle 912 (e.g., a single piece of material defines guide head 908 and handle 912). In some embodiments, handle 912 may be detachable from guide head 908. In the embodiment shown, guide head 908 has a first end 916, an opposing second end 920, an upper side 924, a lower side 928, and a pair of opposing lateral sides 932 extending between upper side 924 and lower side 928. In this embodiment, guide head 908 has a first guide pin channel 936, a second guide pin channel 940, and a saw guide channel 944. In the embodiment shown, guide head 908 comprises a unitary piece but can also comprise multiple guide head pieces that removeably couple to each other, similar to the saw guide embodiment discussed previously. In the embodiment shown, handle 912 has a proximal end 948 and a distal end 952. In the embodiment shown, handle 912 is coupled to a lateral side 932 of guide head 908 and extends away from guide head 908 at an angle from the plane of lateral side 932. In the embodiment shown, handle 912 extends at an acute angle from the plane of lateral side 932.

In the embodiment shown, first guide pin channel 936 extends between upper side 924 and lower side 928 of guide head 908 at first end 916 and second guide pin channel 940 extends between upper side 924 and lower side 928 of guide head 908 at first end 920. As shown, first guide pin channel 936 has a first central axis 956 and second guide pin channel 940 has a second central axis 960. In this embodiment, first central axis 956 and second central axis 960 are vertical and perpendicular to upper side 924 and lower side 928. Saw guide channel 944 extends vertically between and through both upper side 924 and lower side 928. In this embodiment, saw guide channel 944 is open along the length of lower side 928 and extends between upper side 924, lower side 928, first guide pin channel 936, and second guide pin channel 940. In other embodiments, saw guide channel 944 may extend only part of the distance between lower side 928 and upper side 924.

In the embodiment shown, guide head 908 defines one or more slots 964 in one or both lateral sides 932 at lower side 928. In the embodiment shown, a length 968 of slot 964 is greater than a width 972 or a depth 976 of slot 964. In the embodiment shown, the length 968 of slot 964 extends horizontally along lower side 928 of one or more lateral sides 932 and the depth 976 of slot 964 extends between lower side 928 to a blocking surface 980 that defines the top of slot 964 a distance above lower side 928. With a circular saw blade, as shown, part of the blade can extend beyond the ends of slot 964, such that slot 964 need not be longer than (and is thus shorter than) the length of the body for which guide head 908 is adapted to form a slot or recess in a bone. Similarly, the distance between blocking surface 980 corresponds to a height of the plate or implant intended to fit into the slot or recess in the bone.

FIGS. 14A-14G depict various views of stages of the present methods using saw guide 900 with implant 100c. As shown in FIG. 14A, saw guide 900 is positioned to have lower side 928 face (e.g., and abut) a surface of a bone 400 to form a recess 404 (and, in some instances recesses 408). In the embodiment shown, a guide pin 500 is inserted into each of first guide pin channel 936 and second guide pin channel 936. When inserted into the guide pin channels 936, 940, guide pins 500 extend along first central axis 956 and second central axis 960, respectively. As shown, guide pins 500 are inserted into first guide pin channel 936 and second guide pin channel 940 at upper side 924 such that guide pins 500 pass through the guide pin channels and extend from lower side 928. In this embodiment, guide head 908 is configured to move (e.g., slide) up and down along parallel central axes 956, 960.

Figure 14B:
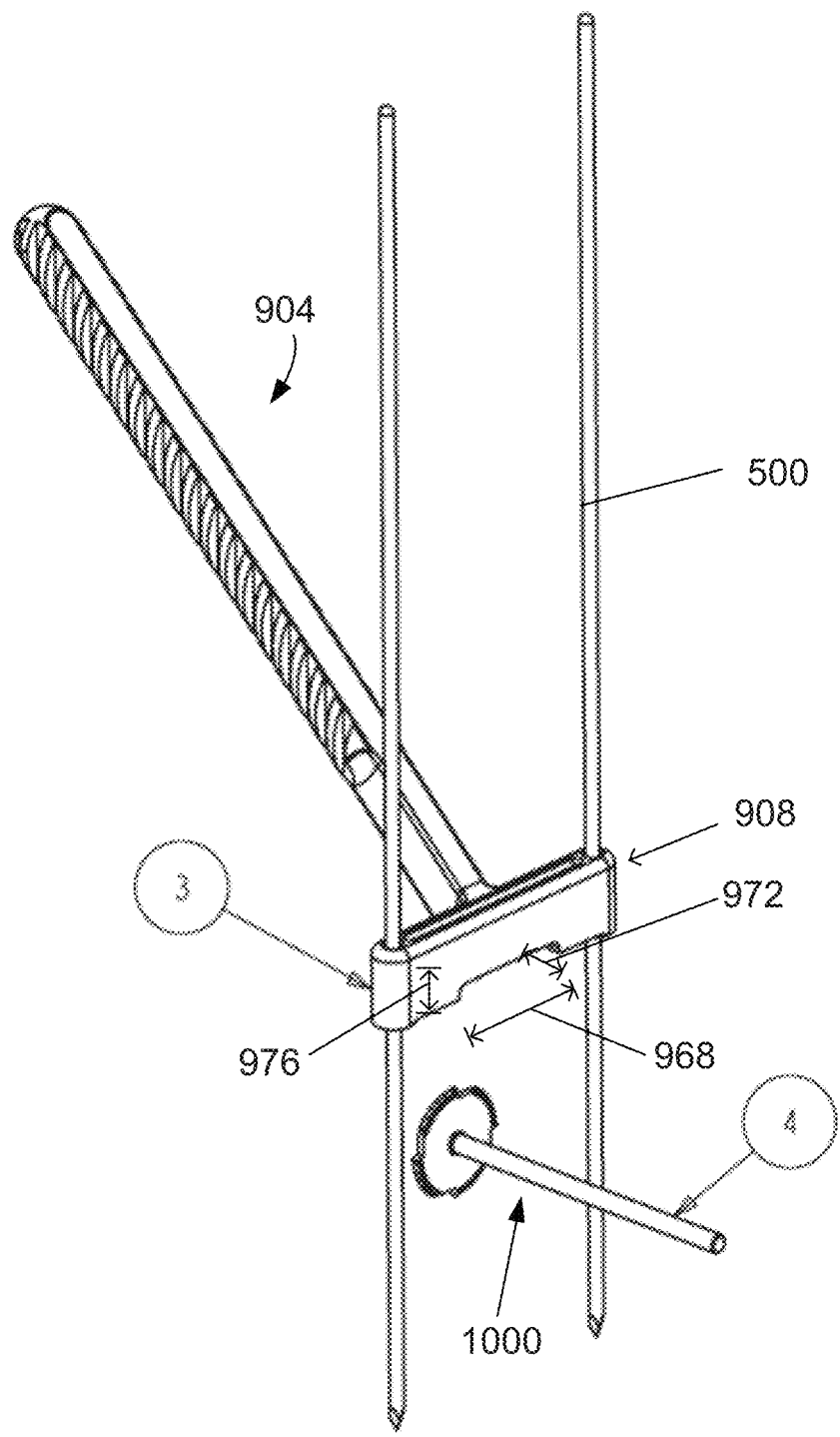
Figure 14C:
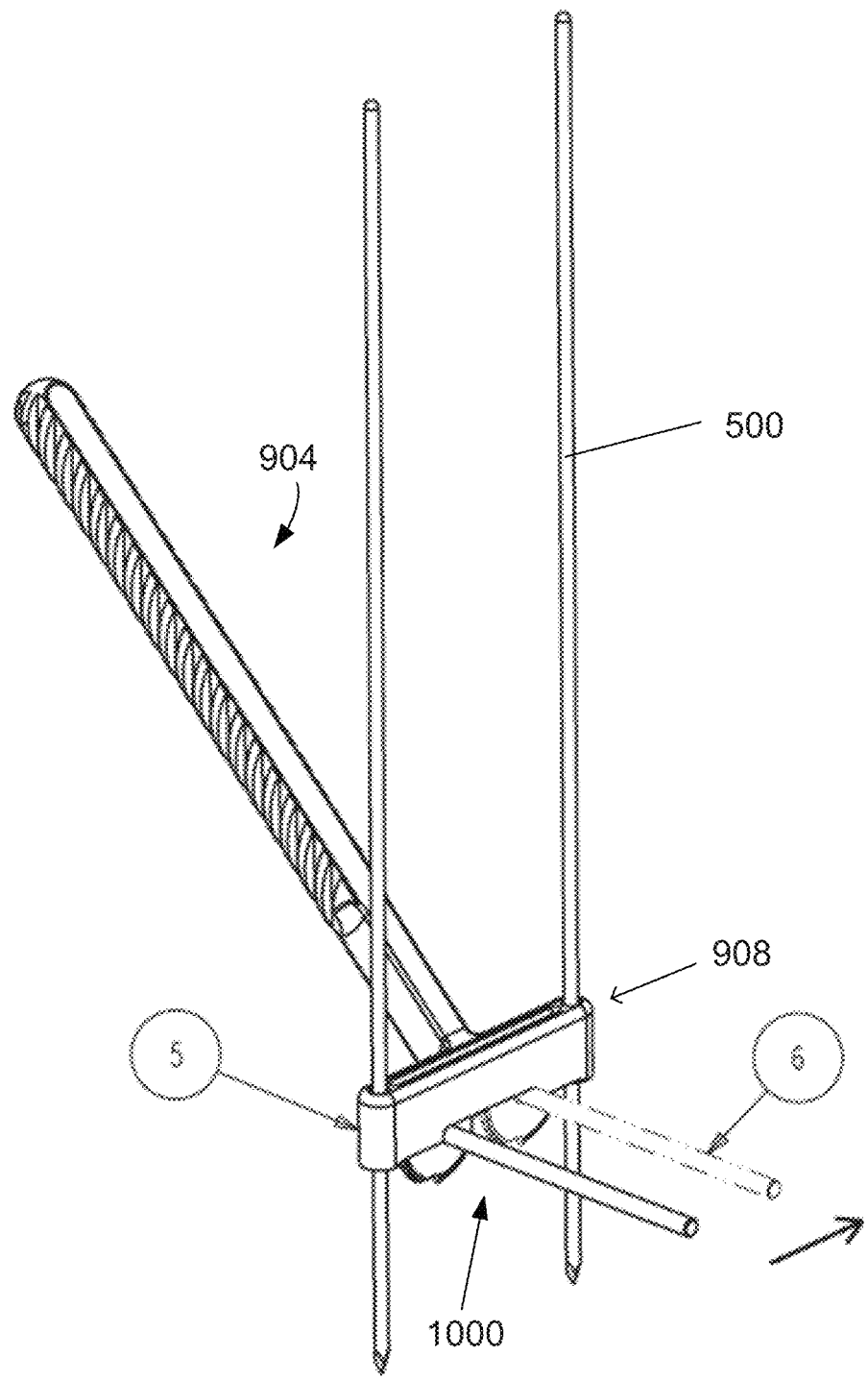

As shown in FIG. 14B-14C, saw blade 1000 (described more fully in FIGS. 15A-15C) is positioned so that cutting edge 1028 of cutting member 1020 is inserted into saw guide channel 944 at lower side 928 of guide head 908. In the embodiment shown, shaft 1004 extends from saw guide channel 944 through lateral side 932 via slot 964. Cutting member 1020 is then moved laterally back and forth within saw guide channel 944 as shaft 1004 (and thereby cutting member 1020) are rotated. As described below, shaft 1004 is rotated around rotational axis 1008 by a drill, other mechanized rotation element, by hand or by other suitable means. Cutting member 1020 is moved within saw guide channel 944 to contact the surface of bone 400. In the embodiment shown, as saw blade 1000 rotates, cutting member 1020 cuts recess 404 to an increasing depth. As the depth of recess 404 increases, guide head 908 can be moved vertically downward along central axes 956, 960 (e.g., such that blocking surface 968 presses downward on shaft 1004) until lower side 928 contacts the surface of bone 400. The depth of slot 960 is sufficient to enable cutting edge 1028 to cut the recess 404 into the surface of the bone 400 to a predetermined and desired depth. When recess 404 has reached the desired depth, guide head 908 can be moved vertically upward along central axes 956, 960 to decouple from guide pins 500. Saw blade 1000 is also removed, leaving guide pins 500 remaining embedded in bone 400. In some embodiments, reamer 600 can be used as shown in FIGS. 5C and 6F to cut recesses 408 into bone 400.

Figure 14D:
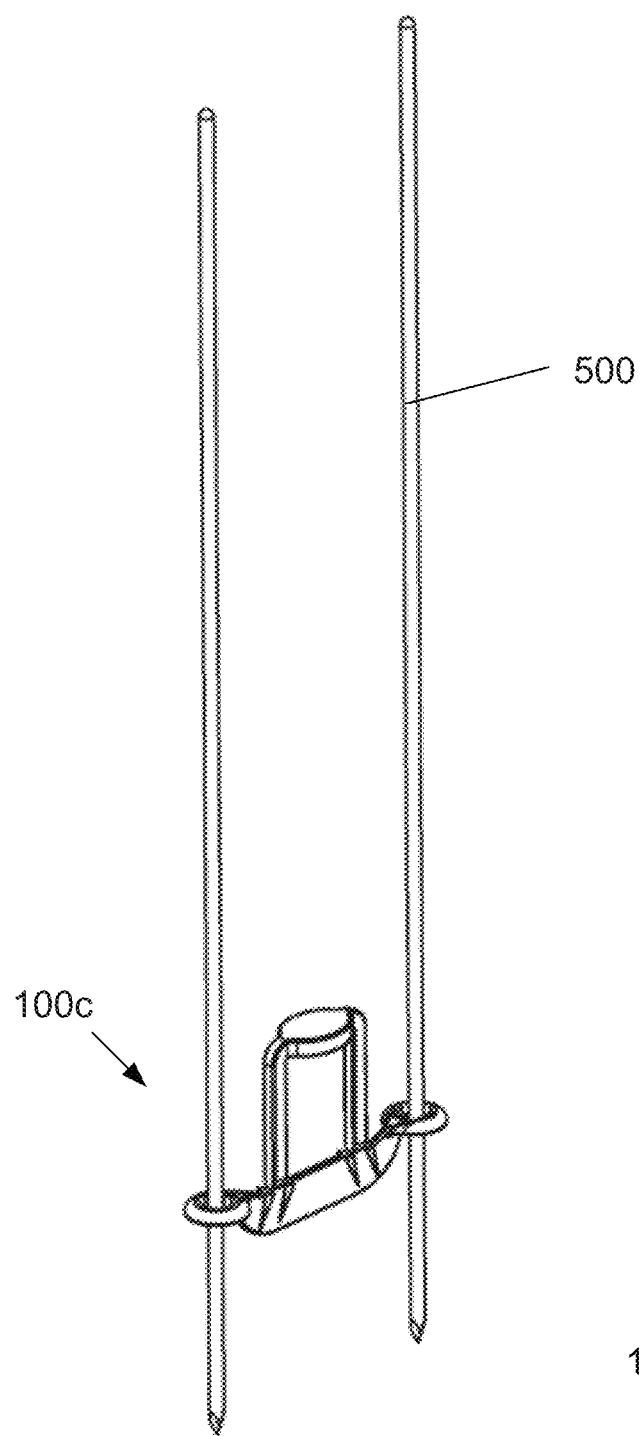
Figure 14E:
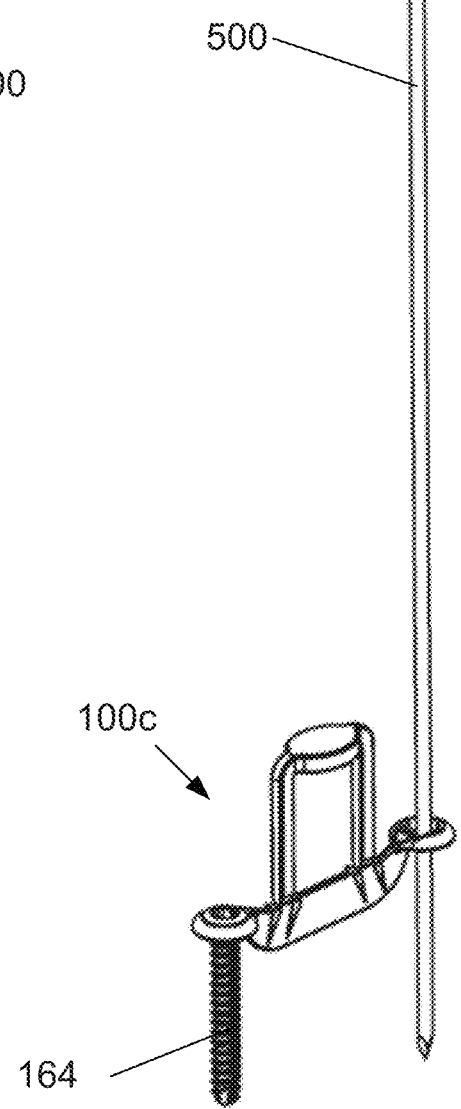
Figure 14F:
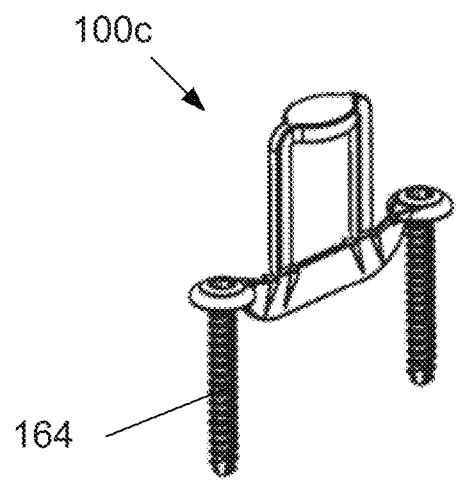
Figure 14G:
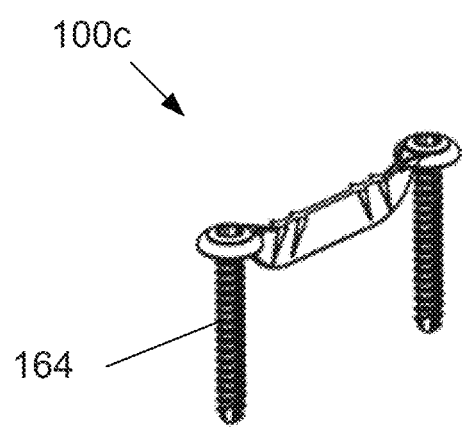

As shown in FIG. 14D, one of the present plates or implants (e.g., 100c) can then be coupled to guide pins 500. First fastener hole 148c and second fastener hole 152c each receive distal end 508 of a guide pin 500 and enable plate 100c to slide along the guide pins until plate 100c reaches a desired position at bone 400. In some embodiments, at least a portion of plate 100c is positioned into recess 404 (and, in some instances, recesses 408) cut into bone 400 as described above. As shown in FIG. 14E, the guide pin 500 passing through first fastener hole 148c is removed and first fastener hole 148c receives a fastener 164 (e.g., along first central axis 956, as shown). As shown in FIG. 14F, in this same way, the other guide pin 500 passing through second fastener hole 152c is removed and second fastener hole 152c receives a fastener 164 (e.g., along second central axis 960 as shown). In some embodiments, fasteners 164 are inserted into a recess 408 cut by reamer 600 to secure plate 100c to the bone 400. As shown in FIG. 14G, when plate 100c is secured by fasteners 164 into bone 400 at the desired position, handle 800a is also removed from plate 100c via detachable joints 844 (e.g., by bending the handle relative to the body to cause the detachable joints to break).

Fasteners 164 can comprise screws, bolts, or other suitable fastening devices. In some embodiments, fasteners 164 comprise locking screws. In these embodiments, fastener holes 148, 152 comprise one or more locking mechanisms that receive one or more locking screws or fastener and enable the locking screws/fasteners to lock into the locking mechanisms via threads or other suitable means. In some embodiments, locking screws are used when permanent stabilization is desired or when the severity or location of a fracture or injured joint requires a higher degree of stabilization. In other embodiments, non-locking fasteners 164 are used when temporary stabilization is desired or when the severity or location of a fracture or injured joint only requires a lower to moderate degree of stabilization. In some embodiments, both locking and non-locking fasteners 164 are used.

Figure 15A:
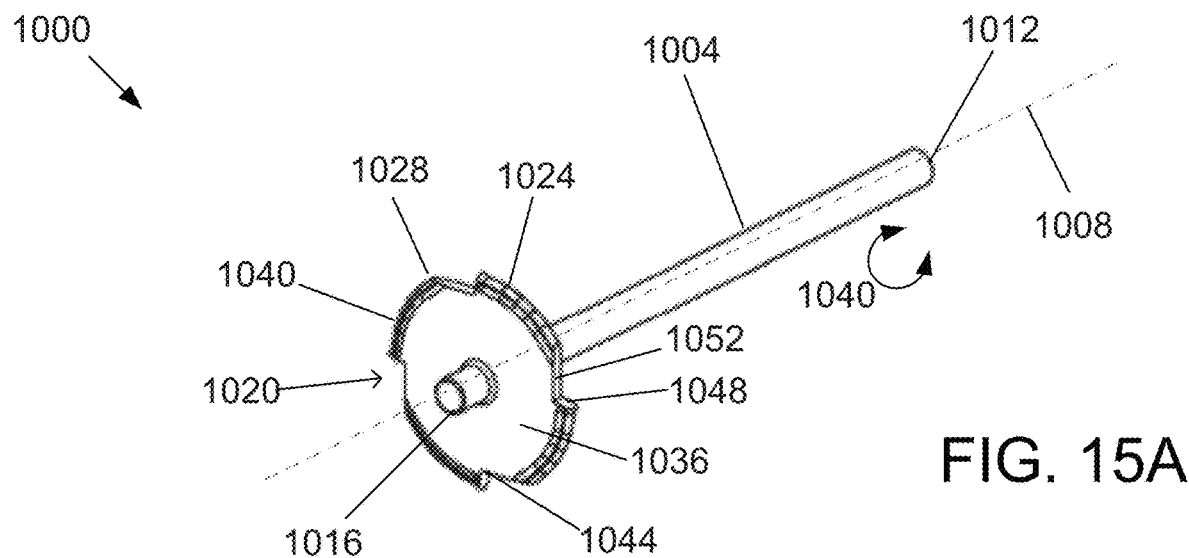
FIGS. 15A-15C depict various views of a second embodiment of a saw blade configured for use with the saw guide of FIGS. 3A-3C or FIGS. 14A-14G.
Figure 15B:
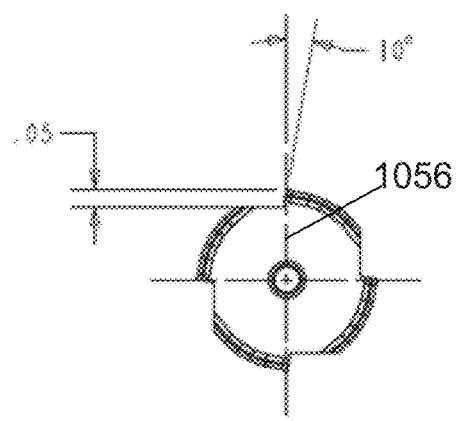
Figure 15C:
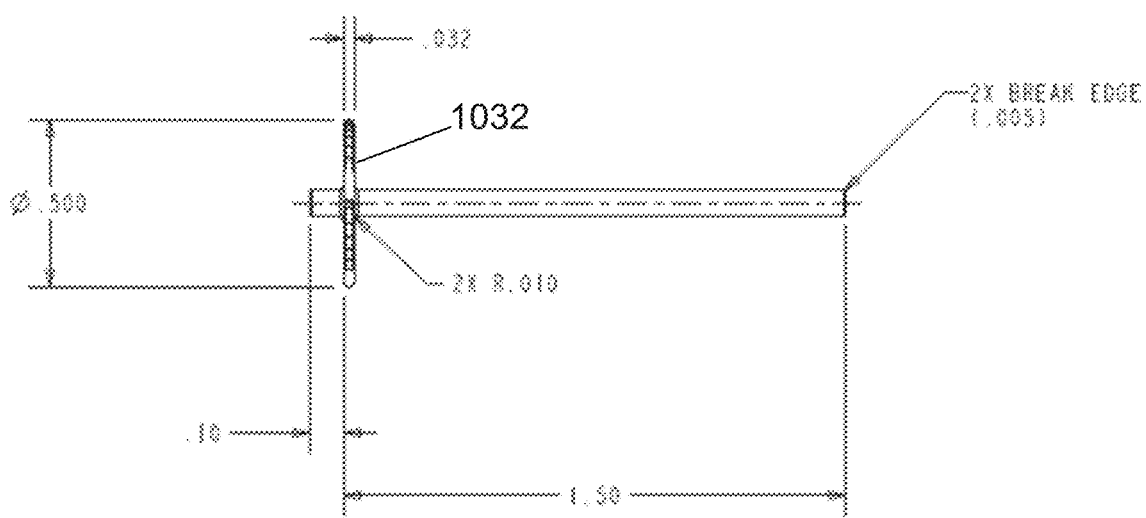

FIGS. 15A-15C depict various views of a second embodiment of the present saw blade 1000 that can be used with saw guide 200 or saw guide 900 disclosed above. In the embodiment shown, saw blade 1000 has a shaft 1004 extending outwardly along a rotational axis 1008. In the embodiment shown, shaft 1004 has a distal end 1012 and a proximal end 1016. In the embodiment shown, saw blade 1000 has a cutting member 1020 having an outer perimeter 1024 with at least one cutting edge 1028 disposed on outer perimeter 1024, an upper side 1032, and a lower side 1036. Saw blade 1000 is configured to be rotated around rotational axis 1008 (e.g., in direction 1040) with cutting edge 1028 in contact with a bone to remove a portion of the bone. In some embodiments, the portion of the bone removed is in a shape of outer perimeter 1024. As shown, outer perimeter 1024 is substantially circular. In this embodiment, cutting edge 1028 comprises a plurality of cutting surfaces 1040 configured to remove bone to create a recess in the bone. In the embodiment shown, cutting edge 1028 includes one or more notches 1044 interrupting the cutting edge to define four smooth outer segments 1048. As shown, notches 1044 each define a respective cutting surface 1040 disposed at an acute angle (e.g., 10 degrees, as shown and labeled in FIG. 15B) relative to a radial line extending from rotational axis 1008 to the inner end of respective cutting surface 1040), and a long edge 1052 that is perpendicular to the radial line extending from rotational axis 1008 to the inner end of respective cutting surface 1040. The small number of notches 1044 and cutting surfaces 1040 results in relatively large notches (relative to similarly sized circular saw blades having a larger number of cutting surfaces) and resulting large size of smooth outer surface segments 1048 reduce skipping of the saw blade when cutting bone, and thereby improve the ability to control the blade. In the embodiment shown, proximal end 1016 of shaft 1004 is coupled to cutting member 1020 at a center of upper side 1032. As shown, cutting member 1020 is disposed in a plane perpendicular to shaft 1004. In the embodiment shown, shaft 1004 extends through cutting member 1020 between upper side 1032 and lower side 1036 and distal end 1012 protrudes a distance out from lower side 1036. FIGS. 15B-15C also include dimensions (in inches) for at least one exemplary configuration of saw blade 1000.

Embodiments of the present plates (e.g., 100), saw guides (e.g., 200), saw blades (e.g., 300), guide pins (e.g., 500), and/or reamers (e.g., 600) can comprise any materials that permit the respective functions described in this disclosure. For example, the present plates, saw guides, reamers, and/or saw blades can comprise at least one of: a biocompatible metal, stainless steel, 316L stainless steel, polymer, and polyphenylsulfone (PPSU) such as Radel®. The present plates can also have a porous surface. Some embodiments of the present device or kit 500 comprise an embodiment of the present plates (e.g., 100), saw guides (e.g., 200), saw blades (e.g., 300), guide pins (e.g., 500), and/or reamers (e.g., 600) and a package within which the plates, saw guide, reamer, and saw blade are sealed. In some such embodiments, one or more of the elements of the kit are sterile.

The present implants and plates can be manufactured via any suitable manufacturing method, such as, for example, 3D printing, injection molding, forging, and/or machining.

For example, in the Direct Metal Printing (DMP) process offered by 3D Systems Leuven (formerly known as LayerWise), a laser is selectively directed to a flat metal powder bed on a building platform to cause the metal particles pinpointed by the laser to melt and attach to the previous layer. Thin cross-section layers are sequentially added and the printed plate gradually evolves toward the targeted geometry. Throughout the printing process, additional metal powder can be supplied to the building platform. The plate can be printed using a number of suitable metals and/or metal alloys and can be used without binders and/or glues.

By way of further example, in the titanium injection molding process offered by Praxis Technology, fine titanium powder and thermoplastic binders are combined at precise, predetermined levels. The powder and binders are mixed together and heated to enable the titanium powder to disperse within the melted binders. The mixture is pelletized to form a feedstock suitable for injection molding. The feedstock is fed from a hopper into a heated barrel where the binders in the feedstock are melted. Once the feedstock is molten, it is injected into a mold to form a piece in the desired geometry. The mold can be in the shape of any of plates described herein previously. Once the piece is cool, the piece is ejected and ready for debinding. A portion of the binder components is removed via solvent extraction and/or catalytic decompression. A debound piece is sintered by being placed on a ceramic setter and loaded into a furnace for high temperature processing. During the early stage of sintering, the remaining portion of the binder components is thermally decomposed. After this initial stage, the piece is heated to a high temperature where densification occurs, resulting in a significant shrinkage of up to 20%. The piece is hot isostatically pressed (HIP) to achieve a 100% density of conventional titanium. Secondary finishing options such as CNC machining, anodizing, passivation, surface finishing, and laser marking are also possible.

By way of further examples, the plate or implant can be traditionally formed (e.g., forging, molding, machining) as a solid metal piece with an open structure, and a coating of suitable material such as hydroxyapatite/titanium (HA/Ti) can be added, the plate or implant can be traditionally formed and the outer surface etched to create a porous surface, and/or the plate or implant can be formed via an additive manufacturing processes such as electron beam manufacturing to create a plate with a porous structure. For example, a cancellous, bone-like, and fully porous titanium foam with an open cell structure can be machined to a desired size and shape (e.g., using wire electrical discharge machining (EDM)) in a hollow shell having (e.g., with a wall thickness of 1-2 mm) and disposed on or filled with a solid core. As another example, a surface texture may be photo-etched onto a surface of the plate or implant.

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present devices, apparatuses, kits, and methods are not intended to be limited to the particular forms disclosed. Rather, they include all modifications and alternatives falling within the scope of the claims, and embodiments other than the one shown may include some or all of the features of the depicted embodiment. For example, body 204 of saw guide 200 can include four slots and/or planar surfaces for guiding a saw blade (e.g., at 4 or more angles). For example, components may be combined as a unitary structure, and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A bone-implant apparatus comprising:
an elongated implant body having a first end and an opposing second end;
a first guide member coupled to the first end of the implant body, the first guide member having a lower bone-facing surface and defining a first fastener hole that extends through the lower bone-facing surface and has a central axis;
a second guide member coupled to the second end of the implant body, the second guide member having a lower bone-facing surface and defining a second fastener hole that extends through the lower bone-facing surface and has a central axis;
where a lower portion of the implant body extends below at least a portion of the lower bone-facing surface of the first guide member and/or below at least a portion of the lower bone-facing surface of the second guide member;
where the first guide member is coupled to the first end of the implant body by a first interface such that a portion of the first guide member overlies a portion of the implant body; and
where the first and second fastener holes are each configured to receive a fastener coaxial with the respective central axis.

2. The apparatus of claim 1, where the lower portion of the implant body extends below the lower bone-facing surfaces of both of the first and second guide members.

3. The apparatus of claim 1, where the implant body has an upper edge, a lower edge opposing the upper edge, a pair of opposing sides extending between the upper and lower edges, a length extending between the first and second ends, a height extending between the upper and lower edges, and a width extending between the opposing sides, where the length of the implant body is greater than the height and the width of the implant body.

4. The apparatus of claim 3, further comprising one or more barbs disposed on one or more of the opposing sides and configured to compress one or more pieces of bone together, where each barb:
is tapered such that a width of the barb is greater at the upper edge of the implant body and decreases as the barb extends toward the lower edge of the implant body; and
extends at an angle away from a lateral plane that bisects the implant body such that a distance between the barb and the lateral plane increases as the barb extends toward the lower edge of the implant body.

5. The apparatus of claim 1, where the central axis of the first fastener hole extends toward a lateral plane that bisects the implant body, and the central axis of the second fastener hole extends toward the lateral plane.

6. The apparatus of claim 1, where at least one of the first and second guide members defines a plurality of fastener holes.

7. The apparatus of claim 1, where:
the central axis of the first fastener hole is substantially parallel to the central axis of the second fastener hole; and
the first guide member is configured to be bent relative to the implant body when the apparatus is secured to a bone, and the second guide member is configured to be bent relative to the implant body when the apparatus is secured to the bone.

8. The apparatus of claim 1, further comprising multiple implant bodies coupled together by a third guide member defining a third fastener hole having a central axis, where the multiple implant bodies extend in a direction of a length of the implant bodies.

9. The apparatus of claim 1, where the second guide member is coupled to the second end of the implant body by a second interface such that a portion of the second guide member overlies a portion of the implant body.

10. The apparatus of claim 1, where a plane that extends through the implant body along a length of the implant body bisects the first fastener hole and the second fastener hole.

11. The apparatus of claim 1, where:
a first plane that extends through a center of the first guide member and the first fastener hole is parallel to a second plane that extends through a center of the second guide member and the second fastener hole; and
the first plane and the second plane are perpendicular to a length of the implant body.

12. The apparatus of claim 1, further comprising a handle comprising at least one vertical attachment member coupled to the implant body and a cross member coupled to the at least one vertical attachment member.

13. The apparatus of claim 12, where:
the cross member has an upper side, a lower side opposing the upper side, and a pair of opposing faces; and
the cross member is curved at the pair of opposing faces.

14. The apparatus of claim 12, further comprising one or more detachable joints disposed between the at least one attachment member and the implant body, the one or more detachable joints configured to detachably couple the handle to the implant body.

15. A kit comprising:
a bone implant apparatus of claim 1; and
a package within which the bone implant apparatus is sealed.

16. A method of modifying a bone, comprising:
positioning a lower side of a guide body of a guide apparatus against a surface of a bone;
inserting guide pins through first and second guide pin channels of the guide body into the bone;
forming a recess in the bone with a saw blade that is disposed in a saw guide channel of the guide body, where a first one of the guide pins that extends through the first guide pin channel is disposed on a first side of a cut or break line in the bone, and a second one of the guide pins that extends through the second guide pin channel is disposed on a second side of the cut or break line in the bone;
decoupling the guide body from the guide pins while the guide pins are inserted into the bone; and
disposing at least a portion of a bone implant apparatus of claim 1 into the recess such that each of the guide pins is received in a respective one of the first and second fastener holes of the bone implant apparatus.

17. The method of claim 16, where the guide apparatus comprises:
the guide body having a first end, a second end opposing the first end, an upper side, the lower side opposing the upper side, and a pair of opposing lateral sides extending between the upper and lower sides, the guide body defining:
the first guide pin channel extending through the lower side of the body,
the second guide pin channel extending through the lower side of the body, and
the saw guide channel extending through the lower side of the body;
where each of the first guide pin channel and the second guide pin channel has a central axis that extends:
toward a lateral plane that bisects the guide body; or
perpendicular to the lower side; and
where the body is configured to be temporarily coupled to the bone by the guide pins extending through the first and second guide pin channels into the bone such that:
the lower side of the guide body faces the bone; and
the saw blade can be guided along the saw guide channel to form a recess in the bone.

18. The method of claim 16, where decoupling the guide body comprises detaching from each other two pieces of the guide body that cooperate to define the first guide pin channel, the second guide pin channel, and the saw guide channel.

19. The method of claim 16, further comprising:
for at least one of the guide pins, rotating a reamer around the guide pin with a proximal cutting end of the reamer in contact with the bone to enlarge an end of the recess.

20. The method of claim 16, further comprising:
removing the guide pins from the bone;
inserting a first fastener through the first fastener hole of the bone-implant apparatus and into a first hole in the bone; and
inserting a second fastener through the second fastener hole of the bone-implant apparatus and into a second hole in the bone, where the first fastener extends through a first part of the bone, across a cut or break line in the bone, and into a second part of the bone and/or the second fastener extends through the second part of the bone, across the cut or break line, and into the first part of the bone.

* * * * *